US008772349B2

(12) United States Patent
Muñoz Blanco et al.

(10) Patent No.: US 8,772,349 B2
(45) Date of Patent: Jul. 8, 2014

(54) CANNABINOID QUINONE DERIVATIVES

(75) Inventors: Eduardo Muñoz Blanco, Córdoba (ES); Giovanni Appendino, Córdoba (ES); María Luz Bellido Cabello De Alba, Córdoba (ES)

(73) Assignee: Vivacell Biotechnology Espana, S.L., Cordoba (ES)

( * ) Notice: Subject to any disclaimer, the term of this patent is extended or adjusted under 35 U.S.C. 154(b) by 14 days.

(21) Appl. No.: 13/636,214

(22) PCT Filed: Mar. 26, 2010

(86) PCT No.: PCT/ES2010/070156
§ 371 (c)(1),
(2), (4) Date: Sep. 20, 2012

(87) PCT Pub. No.: WO2011/117429
PCT Pub. Date: Sep. 29, 2011

(65) Prior Publication Data
US 2013/0158126 A1 Jun. 20, 2013

(51) Int. Cl.
*C07C 50/28* (2006.01)

(52) U.S. Cl.
USPC ............................................. 514/690

(58) Field of Classification Search
None
See application file for complete search history.

(56) References Cited

FOREIGN PATENT DOCUMENTS

| WO | 2005067917 A1 | 7/2005 |
| WO | 2008107878 A1 | 9/2008 |

OTHER PUBLICATIONS

Pohanka et al. Antimicrobial Dialkylresorcinols from *Pseudomonas* sp. Ki19. J. Nat. Prod. 2006, 69, pp. 654-657.*
Pohanka et al. Antimicrobial Dialkylresorcinols From *Pseudomonas* sp. Ki19. J. Nat. Prod. 2006, vol. 69, pp. 654-657.*
Lippard. The art of Chemistry. Nature 2002, vol. 416, p. 587.*
Bernardo, Antoniette, et al.; "Regulation of Glial Cell Functions by PPAR-gamma Natural and Synthetic Agonists," PPAR Research, 2008, pp. 1-10.
Bishop-Bailey, David, "Peroxisome proliferator-activated receptors in the cardiovascular system," British Kournal of Pharmacology, 2000, pp. 823-834, vol. 129.
Bouaboula, Monsif, et al.; "Anandamide induced PPAR gamma transcriptional activation and 3T3-L1 preadipocyte differentiation," European Journal of Pharmacology, 2005, pp. 174-181, vol. 517.
Burstein, Sumner, "PPAR-gamma: A nuclear receptor with affinity for cannabinoids," Life Sciences, 2005, pp. 1674-1684, vol. 77.
Delerive, P., et al.; "Peroxisome proliferator-activated receptors in inflammation control," Journal of Endocrinology, 2001, pp. 453-459, vol. 169.
Fievet, Catherine, et al.; "PPAR alpha and PPAR gamma dual agonists for the treatment of type 2 diabetes and the metabolic syndrome," Current Opinion in Pharmacology, 2006, pp. 606-614, vol. 6.
Fu, Jin, et al.; "Oleylethanolamide regulates feeing and body weight through activation of the nuclear receptor PPAR-alpha," Nature, 2003, pp. 90-93, vol. 425.
Gelman, L., et al.; "Molecular basis of selective PPARgamma modulation for the treatment of Type 2 diabetes," Biochim Biophys Acta, 2007, col. 1771, Abstrat Only.
Hsueh, Willa A., et al.; "Peroxisome Proliferator-Activated Receptor gamma: Implications for Cardiovascular Disease," Hypertension, 2004, pp. 297-305, vol. 43.
Lehmann, Jurgen M., et al.; "An Antidiabetic Thiazolidinedione Is a High Affinity Ligand for Peroxisome Proliferator-activated receptor gamma (PPARgamma)," The Journal of Biological Chemistry, 1995, pp. 12953-12956, vol. 270.
Liu, Jilin, et al.; "Activation and Binding of Peroxisome Proliferator-Activated Receptor gamma by Synthetic Cannabinoid Ajulemic Acid," Molecular Pharmacology, 2003, pp. 983-992, vol. 63.
Lottenberg, Simao Augusto, et al.; "Metabolic syndrome: identifying the risk factors," Jornal de Pediatria, 2007, pp. S204-S208, vol. 83 (5 Suppl.).
Loverme, Jesse, et al.; "Rapid Broad-Spectrum Analgesia through Activation of Peroxisome Proliferator-Activated Receptor-alpha," The Journal of Pharmacology and Experimental Therapeutics, 2006, pp. 1051-1061, vol. 319.
Murphy, Gregory J.; "PPAR-gamma agonists: therapeutic role in diabetes, inflammation and cancer," Trends in Pharmacological Sciences, 2000, pp. 469-474, vol. 21.
O'Sullivan, S.E., et al.; "Cannabinoid activation of peroxisome proliferator-activated receptors: Potential for modulation of inflammatory disease," Immunobiology, 2010, pp. 611-616, vol. 215.
O'Sullivan, S.E., et al; "Time-dependent vascular actions of cannabidiol in rat aorta," European Journal of Pharmacology, 2009, pp. 61-68, vol. 612.
O'Sullivan, S.E., "Cannabinoids go nuclear: evidence for activation of peroxisome proliferator-activated receptors," British Journal of Pharmacology, 2007, pp. 576-582, vol. 152.
Rosen, Evan D., et al.; "Adipocyte differentiation from the inside out," Nat. Rev. Molecular Cell Biology, 2006, pp. 885-896, vol. 7.
Stienstra, Rinke, et al.; "PPARs, Obesity, and Inflammation," PPAR Research, 2007, Article ID 95974, pp. 1-12.
Sun, Yan, et al.; "Cannabinoids: A New Group of Agonists of PPARs," PPAR Research, 2007, Article ID 23513, pp. 1-7.
Szeles, L.; PPARgamma in immunity and inflammation: cell types and diseases, Biochim Biophys Acta, 2007, vol. 1771, Abstract Only.
Tachibana, Keisuke, et al.; "The Role of PPARs in Cancer," PPAR Research, 2008, Article ID 102737, pp. 1-15.
Tontonoz, Peter, et al.; "Fat and Beyond: The Diverse Biology of PPARgamma," Annual Review of Biochemistry, 2008, pp. 289-312, vol. 77.

(Continued)

*Primary Examiner* — Leslie A. Royds Draper
*Assistant Examiner* — Taina D Matos Negron
(74) *Attorney, Agent, or Firm* — Tristan A. Fuierer; Moore & Van Allen PLLC

(57) ABSTRACT

Cannabinoid quinone derivatives. The present invention refers to cannabinoid quinone derivatives to be used as medicaments, particularly as PPAR gamma (PPARg) agonists for treating diseases which etiology is based on an impaired PPARg function as transcription factor i.e. PPARg-related diseases.

8 Claims, 10 Drawing Sheets

(56) References Cited

OTHER PUBLICATIONS

Vanden, Berghe W., et al.; "A paradigm for gene regulation: inflammation, MF-kappaB and PPAR," Adv Exp Med Biol., 2003, pp. 181-196, vol. 544; Abstract Only.
International Search Report, Jan. 2, 2011.
Database Beilstein, Beilstein Institute for Organic Chemistry, 1913, XP002611705, Abstract.
Database Beilstein, Beilstein Institute for Organic Chemistry, 2006, XP002611706, Abstract.
Database CAPLUS, Chemical Abstracts Service, 1973, XP002611707, Abstract.
Czekelius, C., "Stichwort: aliphatische Verbindungen," http://www.roempp.com/prod/, 2009, XP002611708.

* cited by examiner

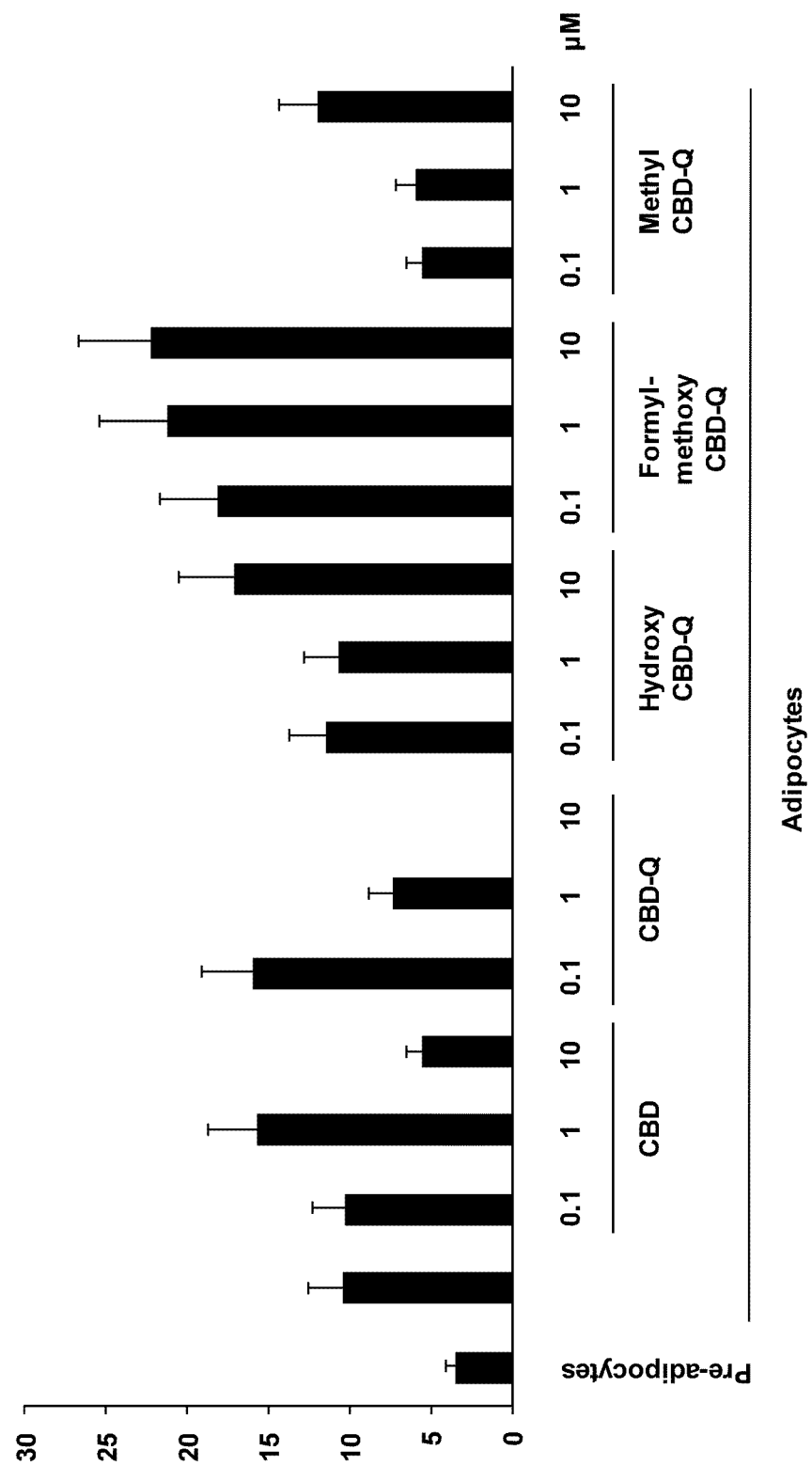

CANNABINOID QUINONE DERIVATIVES

CROSS-REFERENCE TO RELATED APPLICATIONS

This application is filed under the provisions of 35 U.S.C. §371 and claims the priority of International Patent Application No. PCT/ES2010/070156 filed on 26 Mar. 2010 entitled "Cannabinoid Quinone Derivatives" in the name of Eduardo MUÑOZ BLANCO, et al, which is hereby incorporated by reference herein in their entirety.

FIELD OF THE INVENTION

The present invention refers to cannabinoid quinone derivatives to be used as medicaments, particularly as Peroxisome Proliferator-activated Receptor gamma (PPARg) agonists for treating diseases which etiology is based on an impaired PPARg function as transcription factor i.e. PPARg-related diseases.

Due to the almost ubiquitous expression of the PPARg in different tissues, the present invention may be encompassed in the medical field, in general, and, more specifically, in that field of the medicine dealing with the treatment of diseases, sharing the above mentioned etiology, by exerting an agonistic effect over PPARg.

STATE OF THE ART

PPARg is a member of the PPAR subfamily of nuclear hormone receptors which are ligand-inducible transcription factors. PPARs form heterodimers with their obligate partner retinoid X receptor (RXR). All PPAR isotypes have a similar domain organization: the N-terminal A/B domain contains a putative ligand-independent transcription activation function 1 (AF-1). The DNA-binding C domain, composed of two zinc fingers, binds to the peroxisome proliferator response element (PPRE) in the regulatory region of PPAR target genes. The D domain is a hinge region that confers flexibility between the C domain and the E domain (ligand-binding domain or LBD) that contains the ligand-dependent transcription activation function 2 (AF-2). The transcriptional activity of PPARs is regulated not only by their ligands, but also by post-translational modifications such as phosphorylation.

PPARg is expressed in a range of tissues including skeletal muscle cells, osteoclasts, osteoblasts, several immune-type cells, and in the brain and peripheral nervous system. Adipose tissue exhibits the highest levels of PPARg expression in the human body.

PPARg is of special interest because it is involved in the regulation of adipocyte formation, insulin sensitivity and inflammation (Fievet et al. 2006; Stienstra et al. 2007; Tontonoz and Spiegelman, 2008). It is clear that PPARg is the dominant or "master" regulator of adipogenesis, due to the fact that is both sufficient and necessary for fat cell differentiation. The regulatory regions of a large number of genes that play important roles in lipogenesis and insulin sensitivity contain binding sites for PPARg, including aP2, LPL, adiponectin, and Glut4 (Rosen and MacDougald, 2006).

On the other hand, activation of PPARs exerts anti-inflammatory activities in several cell types by inhibiting the expression of pro-inflammatory genes, thereby reducing the production of cytokines, metalloproteases and acute-phase proteins. It also acts increasing anti-inflammatory cytokines, and inhibiting inducible nitric oxide synthase (iNOS) expression (see Széles et al., 2007 for a recent review). PPARs negatively regulate the transcription of inflammatory response genes by antagonizing the AP-1, nuclear factor-kappaB (NF-KB), signal transducer and activator of transcription (STAT) and nuclear factor of activated T-cells (NFAT) signaling pathways (Vanden Berghe et al. 2003). Importantly, PPARs also stimulate the catabolism of pro-inflammatory eicosanoids (Delerive et al. 2001).

PPARg has been recognized as playing a fundamentally important role in the immune response through its ability to inhibit the expression of inflammatory cytokines and to direct the differentiation of immune cells towards anti-inflammatory phenotypes (Tontonoz and Spiegelman, 2008).

The anti-inflammatory effects of PPARg are closely linked with its anti-diabetic effects. Ligand activation of PPARg in adipocytes is associated with decreased production of proteins termed adipokines (TNFα, IL-6, resistin, etc.), which are postulated to cause insulin resistance. Therefore, activation of PPARg in adipose tissue impacts whole-body insulin sensitivity by altering the production of adipokines. That is the reason why activators of PPARg such as the thiazolidinediones (TZDs, e.g rosiglitazone, piaglitazone) are used clinically in the treatment of type 2 diabetes (Lehmann et al., 1995).

In addition, PPARg agonists have been shown to have positive cardiovascular effects, which include increased availability of nitric oxide, reductions in blood pressure and attenuation of atherosclerosis (Bishop-Bailey, 2000; Hsueh and Bruemmer, 2004).

Therefore, PPARg agonists are suitable treatment for a cluster of metabolic abnormalities, termed metabolic syndrome as a whole and which include elevated blood pressure, elevated triglycerides, low high-density lipoprotein cholesterol (HDL-C), abdominal obesity, inflammation, insulin resistance, and elevated blood glucose (Lottenberg et al., 2007; Murphy and Holder, 2000). Metabolic syndrome has as main cause the insulin resistance, which is secondary to excess abdominal or visceral adipose tissue.

Interestingly, PPARg agonists have shown anti-inflammatory and neuroprotective effects in several experimental models of Parkinson's diseases, amyotrophic lateral sclerosis, multiple sclerosis and stroke, as well as in a few clinical studies (Bernardo and Minghetti, 2008).

Additionally, PPARg must formally be considered a tumor suppressor gene in the genetic sense. It is expressed in a variety of tumor cells, and the activation of PPARg by ligands led to either inhibition of cell proliferation or induction of apoptosis (Tachibana et al., 2008; Tontonoz and Spiegelman, 2008).

The beneficial effects of PPARg activation can be used for the treatment of several diseases, as is shown in Table 1. This table summarizes the actions of PPARs in inflammatory diseases. Abbreviations: ↓ inhibition, ↑ stimulation, hepatic stellate cells (HSC), vascular smooth muscle cells (VSMC), monocyte chemoattractant protein-1 (MCP-1), T-helper (Th), tumor necrosis factor-α (TNFα), cyclooxygenase (COX), interferon-gamma (INFγ), inducible nitric oxide synthase (iNOS), intracellular adhesion molecule-1 (ICAM-1). Adapted from Kostadinova et al., 2005.

TABLE 1

| Disease | Effect of PPARγ and its ligands |
|---|---|
| Atherosclerosis | ↓Recruitment of immune cells. |
|  | ↓Migration and proliferation of VSMC. |

TABLE 1-continued

| Disease | Effect of PPARγ and its ligands |
|---|---|
| Inflammatory bowel diseases | ↓IL-1β-induced IL-8 and MCP-1 in colonic epithelial cells.<br>Modulation of inflammatory response: ↓Th1 and ↑Th2.<br>Improvement of colitis in mice models.<br>Improvement of colitis in 4/15 patients. |
| Rheumatoid arthritis | ↑Synoviocyte and chrondrocyte apoptosis.<br>↓TNFα, IL-1β and COX-2 in rheumatoid synoviocytes.<br>Improvement of arthritis in mouse models |
| Liver fibrosis | ↓HSC activation.<br>↓Kupffer cell activation. |
| Nephropathy | ↓IL-1β, MCP-1, COX-2, iNOS, proliferation and ↑apoptosis in mesangial cells.<br>Improvement of micro-albuminuria in Type II diabetic patients and diabetic rats. |
| Psoriasis and skin wound healing | Improvement of psoriatic lesions in mouse models and patients. |
| Pancreatitis | ↓COX-2, ICAM-1 and IL-6 production in pancreas.<br>↓Activation of immune cells.<br>↓Development of chronic pancreatitis in mouse models. |
| Gastritis | ↓TNFα, iNOS, IL-1β, COX-2 and apoptosis in gastric mucosa.<br>Improvement of gastritis in mouse models. |
| Neurodegenerative disorders | ↓iNOS, TNFα, IL-1β, IL-6, INFγ, MCP-1 and COX-2 in astrocytes and microglia.<br>↓Neuronal apoptosis. |
| Cancer | ↑Apoptosis and ↓proliferation of cancer cells.<br>↓Colitis-related colon cancer in mouse models. |

It is generally recognized that there are several side effects associated with PPARg ligands, including weight gain, edema and increased plasma lipoproteins (Gelman et al., 2007). New PPARg agonists that do not possess these side effects are currently being investigated, and it is suggested that partial or low affinity agonists may be beneficial (Gelman et al., 2007).

Direct binding of cannabinoids to PPARs has been demonstrated in several studies throughout reporter gene assays or 3T3-L1 adipogenesis assays. These includes oleylethanolamide (Fu et al., 2003), ajulemic acid (Liu et al., 2003; Burstein, 2005), 2-arachidonoylglycerol (Burstein, 2005), anandamide (Bouaboula et al., 2005), WIN55212-2, noladin ether and virodhamine (Sun et al., 2007), Δ⁹-THC (O'Sullivan et al., 2005), and CBD (O'Sullivan et al., 2009). Some of them have been described to interact with PPARg LBD domain (Liu et al. 2003; O'Sullivan et al., 2009). Nevertheless, PPAR activation is not common to all cannabinoids (LoVerme et al., 2006; Bouaboula et al., 2005; Fu et al., 2003). The PPAR activation by cannabinoids has been subject of some reviews (O'Sullivan and Kendall, 2009; Burstein, 2005; O'Sullivan, 2007; Sun and Bennett, 2007). However, quinone derivative of cannabinoids have been never reported for PPARg activity.

As shown in the comparative examples carried out in the present invention, unfortunately most of those known PPARg agonists, particularly some cannabinoid derivatives, exhibit a low efficiency of binding to PPARg and therefore a reduced PPARg agonistic effect. Moreover, even worse, some of them show high toxicity in several cellular types (cytotoxicity).

Therefore, bearing in mind the ubiquitous disposition of the PPARg in tissues, and consequently the high amount of PPARg related diseases that exist, the development of synthetic PPARg agonists, with a higher efficiency of binding to PPARg as compared with known PPARg agonists and consequently being able to exert a higher PPARg agonistic effect, both in vitro and in vivo, would be of utmost importance and help for improving the condition of patients suffering from PPARg-related diseases. Moreover it would be desirable that those PPARg agonists exhibit low toxicity in cells (low citoxicity).

Present invention gives a new step forward, in the direction of the solution of the above problem, developing novel compounds suitable for treating PPARg-related diseases due to their high PPARg agonistic effect and low cytotoxicity.

DESCRIPTION OF THE INVENTION

The present invention is focused on the formulation of cannabinoid derivatives, particularly cannabinoid quinone (Q) derivatives, synthesized departing from natural cannabinoids such as CBD (cannabidiol) and CBG (cannabigerol) by means of the substitution of some specific radicals.

The compounds of the present invention are cannabinoid quinone (Q) derivatives of Formula (I):

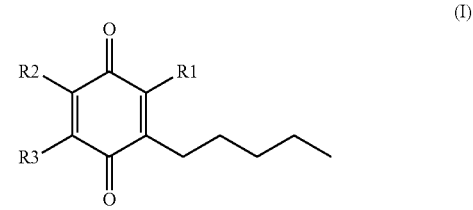

wherein
R1 means hydrogen, hydroxyl, methyl or an aldehyde group,
R2 means a cyclohexene derivative or an aliphatic compound, preferably an alkene,
and R3 means hydroxyl or methyloxy group,
excepting the compound of formula (II)

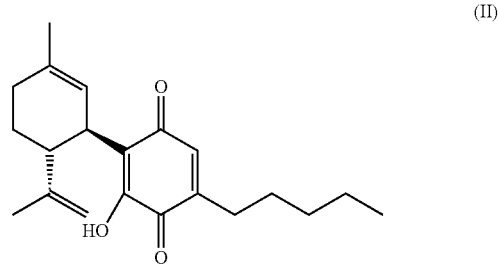

In a preferred embodiment the compounds of the invention are those of Formula (III), (IV), (V) and (VI):

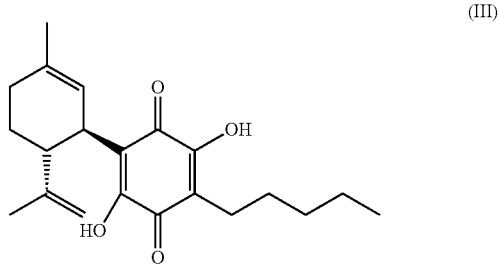

Hydroxy-CBD-Q (H-CBD-Q)

-continued

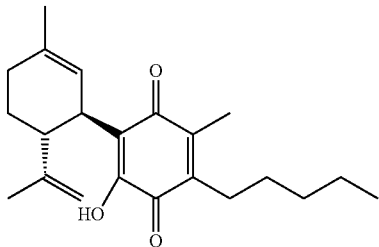

Methyl-CBD-Q (M-CBD-Q) (IV)

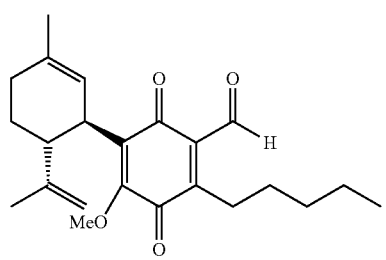

Formyl-Methoxy-CBD-Q (FM-CBD-Q) (V)

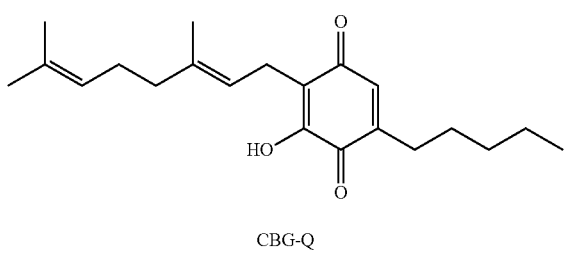

CBG-Q (VI)

As it will be inferred below from the examples and figures, the quinone group (Q) comprised in the general Formula I confers the compounds of the present invention the capacity of binding directly to PPARg, those compounds being good PPARg agonist candidates. Moreover, the present invention also shows that said capacity of binding directly to PPARg is even more efficient when the compounds have a formula comprising said quinone group in combination with the radicals R1, R2 and R3 cited above, this compounds also showing a valuable low cytotoxicity level in several cellular lines as compared with the compounds comprised in the state of the art.

As shown in FIGS. 1 and 2, the compounds of the invention, particularly CBG-Q binds directly to PPARg, having an $IC_{50}$ value of 2,2 and thus much lower than the $IC_{50}$ value of the known compound CBD-Q and CBN. This conclusion shown in FIGS. 1 and 2 is ratified also by the FIG. 3, showing that CBG-Q is able to induce the PPARg activation with higher efficiency than CBG (FIG. 3B) and also than CBD and CBD-Q (FIG. 3A). The stimulation of the differentiation of fibroblasts to adipocytes is a well-known property of PPARg ligands and this function was clearly carried out by CBG-Q which, as shown in FIG. 4, was able to stimulate the differentiation of fibroblasts to adipocytes in a stronger way than CBG.

Moreover, as shown in FIG. 8A, CBD-Q derivates of the invention (M-CBD-Q, H-CBD-Q and FM-CBD-Q) are able to induce the PPARg activation with higher efficiency than CBD-Q, FM-CBD-Q showing the highest PPARg activation values. Additionally, FIG. 8B confirms that the chemical modifications introduced in CBD-Q (M-CBD-Q, H-CBD-Q and FM-CBD-Q) maintained or, in the case of FM-CBD-Q even increased, PPARg affinity. Those results was confirmed in cell cultures, examining the ability to stimulate fat cell differentiation in 3T3L1 fibroblasts, showing that CBD-Q derivatives (M-CBD-Q, H-CBD-Q and FM-CBD-Q), particularly FM-CBD-Q, stimulated the differentiation of fibroblasts to adipocytes in a stronger way than CBD and CBD-Q, and without the cytotoxic effect observed for CBD-Q (see Example 7) at concentration higher than 1 µM (FIG. 8C).

All data inferred from the FIGS. 1 to 4 and 8 shows that M-CBD-Q, H-CBD-Q, FM-CBD-Q and CBG-Q are PPARg ligands capable of binding to PPARg and increasing its transcriptional activity in a more efficient way as compared with known compounds (CBD-Q and CBN).

Therefore the compounds of the invention can be used as PPARg agonists for treating diseases which etiology is based on an impaired PPARg function as transcription factor (PPARg-related diseases) such as, by way of example, metabolic diseases (hypertension, hypertrigliceridemia, hypercholesterolemia (HDL-C), obesity), inflammatory diseases (see Table 1) (atherosclerosis, inflammatory bowel diseases, rheumatoid arthritis, liver fibrosis, nephropathy, psoriasis, skin wound healing, skin regeneration, pancreatitis, gastritis, neurodegenerative disorders and cancer), type II diabetes (insulin resistance) or elevated blood glucose.

As shown in FIG. 5, CBG and CBG-Q have positive effect as anti-inflammatory compounds on adipose tissue and, therefore, are suitable as PPARg agonists for treating type II diabetes by way of decreasing the insulin resistance. Moreover, as elucidated in FIG. 6, both compounds CBG and CBG-Q were able to increment the glucosa uptake both in presence and absence of insulin, but CBG-Q showing a higher effect than CBG in absence of insulin. Thus, although both CBG and CBG-Q are suitable as PPARg agonists for treating type II diabetes by way of decreasing the insulin resistance, CBG-Q is particularly preferred because it can be used for treating type II diabetes by way of decreasing the insulin resistance through reducing pro-inflammatory adipose tissue conditions and also through incrementing the glucose uptake, also in absence of insulin, without having the additional effect on osteoporosis development observed when known compounds such as TZD rosiglitazone is employed (FIG. 7). Moreover, FM-CBD-Q was also confirmed as being able to increment the glucose uptake in presence of insulin (FIG. 9).

Therefore the compounds of the invention are particularly suitable as PPARg agonists particularly for treating inflammatory diseases (see Table 1 of the state of the art), metabolic diseases and type II diabetes.

Although all compounds of the invention showed good properties as PPARg agonists, and therefore none of them should be disregarded, CBG-Q and FM-CBD-Q are particularly preferred because of their incremented PPARg activity both in vitro and in vivo, as well as because of their improved effect on insulin sensitivity, and also by their low cytotoxicity.

The compounds of the invention also comprise their derivatives, analogs, tautomeric forms, stereoisomers, polymorphs, metabolic analogues, pharmaceutically acceptable salts, pharmaceutically acceptable solvates, and compositions containing the same.

Thus, the compounds of the invention can be used alone or formulated in compositions, particularly pharmaceutical compositions, along with another active principles (for example another cannabinoid derivatives) or excipients such as: cosolvents, surfactants, oils, humectants, emollients, preservatives, stabilizers and antioxidants. Any pharmacologically acceptable buffer may be used, e.g., TRIS or phosphate buffers.

Typical compositions include the compounds of the invention, or derivatives thereof, associated with pharmaceutically acceptable excipients which may be a carrier or a diluent. Such compositions can be in the form of a capsule, sachet, paper or other container. In making the compositions, conventional techniques for the preparation of pharmaceutical compositions may be used. For example, the compound of interest will usually be mixed with a carrier, or diluted by a carrier, or enclosed within a carrier which may be in the form of an ampule, capsule, sachet, paper, or other container. When the carrier serves as a diluent, it may be solid, semi-solid, or liquid material which acts as a vehicle, excipient, or medium for the active compound. The compound of interest can be adsorbed on a granular solid container for example in a sachet. Some examples of suitable carriers are water, salt solutions, alcohols, polyethylene glycols, polyhydroxyethoxylated castor oil, peanut oil, olive oil, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose, and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, salt for influencing osmotic pressure, buffers and/or coloring substances and the like, which do not deleteriously react with the active compounds.

The route of administration may be any route, which effectively transports the compound of interest to the appropriate or desired site of action, such as oral, nasal, pulmonary, transdermal or parenteral, e.g., rectal, subcutaneous, intravenous, intraurethral, intramuscular, intranasal, ophthalmic solution or an ointment.

For nasal administration, the preparation may contain the compound of interest dissolved or suspended in a liquid carrier, in particular an aqueous carrier, for aerosol application. The carrier may contain additives such as solubilizing agents, e.g., propylene glycol, surfactants, absorption enhancers such as lecithin (phosphatidylcholine) or cyclodextrin, or preservatives such as parabens.

To prepare topical formulations, the compound interest is placed in a dermatological vehicle as is known in the art. The amount of the compound of interest to be administered and the compound's concentration in the topical formulations depend upon the vehicle, delivery system or device selected, the clinical condition of the patient, the side effects and the stability of the compound in the formulation. Thus, the physician employs the appropriate preparation containing the appropriate concentration of the compound of interest and selects the amount of formulation administered, depending upon clinical experience with the patient in question or with similar patients.

For ophthalmic applications, the compound of interest is formulated into solutions, suspensions, and ointments appropriate for use in the eye. The concentrations are usually as discussed above for local preparations.

For oral administration, either solid or fluid unit dosage forms can be prepared. For preparing solid compositions such as tablets, the compound of interest is mixed into formulations with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers.

Capsules are prepared by mixing the compound of interest with an inert pharmaceutical diluent and filling the mixture into a hard gelatin capsule of appropriate size. Soft gelatin capsules are prepared by machine encapsulation of a slurry of the compound of interest with an acceptable vegetable oil, light liquid petrolatum or other inert oil. Fluid unit dosage forms for oral administration such as syrups, elixirs and suspensions can be prepared. The water soluble forms can be dissolved in an aqueous vehicle together with sugar, aromatic flavoring agents and preservatives to form a syrup. An elixir is prepared by using a hydroalcoholic (e.g., ethanol) vehicle with suitable sweeteners such as sugar and saccharin, together with an aromatic flavoring agent. Suspensions can be prepared with an aqueous vehicle with the aid of a suspending agent such as acacia, tragacanth, methylcellulose and the like.

Appropriate formulations for parenteral use are apparent to the practitioner of ordinary skill, such as the use of suitable injectable solutions or suspensions. The formulation, which is sterile, is suitable for various topical or parenteral routes including intra-dermal, intramuscular, intravascular, and subcutaneous.

In addition to the compound of interest, the compositions may include, depending on the formulation and mode of delivery desired, pharmaceutically-acceptable, non-toxic carriers or diluents, which include vehicles commonly used to form pharmaceutical compositions for animal or human administration. The diluent is selected so as not to unduly affect the biological activity of the combination.

Examples of such diluents which are especially useful for injectable formulations are water, the various saline, organic or inorganic salt solutions, Ringer's solution, dextrose solution, and Hank's solution. In addition, the pharmaceutical composition or formulation may include additives such as other carriers; adjuvants; or non-toxic, non-therapeutic, non-immunogenic stabilizers and the like.

Furthermore, excipients can be included in the formulation. Examples include cosolvents, surfactants, oils, humectants, emollients, preservatives, stabilizers and antioxidants. Any pharmacologically acceptable buffer may be used, e.g., tris or phosphate buffers. Effective amounts of diluents, additives, and excipients are those amounts which are effective to obtain a pharmaceutically acceptable formulation in terms of solubility, biological activity, etc.

The compound of interest maybe incorporated into a microsphere. The compound of interest can be loaded into albumin microspheres, form which it is possible to recover such microspheres in a dry powder for nasal administration. Other materials suitable for the preparation of microspheres include agar, alginate, chitosan, starch, hydroxyethyl starch, albumin, agarose, dextran, hyaluronic acid, gelatin, collagen, and casein. The microspheres can be produced by various processes known to the person skilled in the art such as a spray drying process or an emulsification process.

For example, albumin microspheres can be prepared by adding rabbit serum albumin in phosphate buffer to olive oil with stirring to produce water in oil emulsion. Glutaraldehyde solution is then added to the emulsion and the emulsion stirred to cross-link the albumin. The microspheres can then be isolated by centrifugation, the oil removed and the spheres washed, e.g., with petroleum ether followed by ethanol. Finally, the microspheres can be sieved and collected and dried by filtration.

Starch microspheres can be prepared by adding a warm aqueous starch solution, e.g., of potato starch, to a heated solution of polyethylene glycol in water with stirring to form an emulsion. When the two-phase system has formed (with the starch solution as the inner phase) the mixture is then cooled to room temperature under continued stirring whereupon the inner phase is converted into gel particles.

These particles are then filtered off at room temperature and slurried in a solvent such as ethanol, after which the particles are again filtered off and laid to dry in air.

The microspheres can be hardened by well known cross-linking procedures such as heat treatment or by using chemical cross-linking agents. Suitable agents include dialdehydes, including glyoxal, malondialdehyde, succinicaldehyde, adipaldehyde, glutaraldehyde and phthalaldehyde, diketones such as butadione, epichlorohydrin, polyphosphate, and borate. Dialdehydes are used to cross-link proteins such as albumin by interaction with amino groups, and diketones form schiff bases with amino groups. Epichlorohydrin activates compounds with nucleophiles such as amino or hydroxyl to an epoxide derivative.

The term "unit dosage form" refers to physically discrete units suitable as unitary dosages for subjects, e.g., mammalian subjects, e.g. humans, dogs, cats, and rodents, each unit containing a predetermined quantity of active material calculated to produce the desired pharmaceutical effect in association with the required pharmaceutical diluent, carrier or vehicle. The specifications for the unit dosage forms of this invention are dictated by and dependent on (a) the unique characteristics of the active material and the particular effect to be achieved and (b) the limitations inherent in the art of compounding such an active material for use in humans and animals. Examples of unit dosage forms are tablets, capsules, pills, powder packets, wafers, suppositories, granules, cachets, teaspoonfuls, tablespoonfuls, dropperfuls, ampoules, vials, aerosols with metered discharges, segregated multiples of any of the foregoing, and other forms as herein described. The compositions can be included in kits, which can contain one or more unit dosage forms of the composition and instructions for use to treat one or more of the disorders described herein.

Slow or extended-release delivery systems, including any of a number of biopolymers (biological-based systems), systems employing liposomes, colloids, resins, and other polymeric delivery systems or compartmentalized reservoirs, can be utilized with the compositions described herein to provide a continuous or long term source of therapeutic compound. Such slow release systems are applicable to formulations for delivery via topical, intraocular, oral, and parenteral routes.

An effective amount of the compound of interest is employed in treatment. The dosage of compounds used in accordance with the invention varies depending on the compound and the condition being treated for example the age, weight, and clinical condition of the recipient patient. Other factors include: the route of administration, the patient, the patient's medical history, the severity of the disease process, and the potency of the particular compound. The dose should be sufficient to ameliorate symptoms or signs of the disease treated without producing unacceptable toxicity to the patient. In general, an effective amount of the compound is that which provides either subjective relief of symptoms or an objectively identifiable improvement as noted by the clinician or other qualified observer.

The compounds in this invention can also be given orally in combination with natural or synthetic compounds that bind to or modify the activity of the vitamin D receptor or in combination with compounds that bind to or modify the activity of the retinoid X receptor to provide for a synergistic effect in the treatment or prevention of the disorders. Examples of such compounds that provide for synergistic effect when given in combination with the drugs encompassed by the current invention include vitamin D analogs, various retinoic acid derivatives, and other activators for retinoid X receptors or retinoic acid receptors including but not limited to compounds such as LG100268, tazarotene, TTNPB, AGN 190121, adapalene, or LGD1069 (Targretin).

Therefore the present invention refers to compounds of Formula (I) or derivatives thereof:

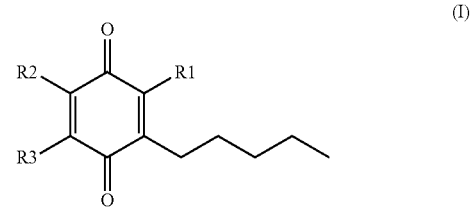

wherein
R1 means hydrogen, hydroxyl, methyl or an aldehyde group,
R2 means a cyclohexene derivative or an aliphatic compound, preferably an alkene,
and R3 means hydroxyl or methyloxy group,
excepting the compound of formula (II)

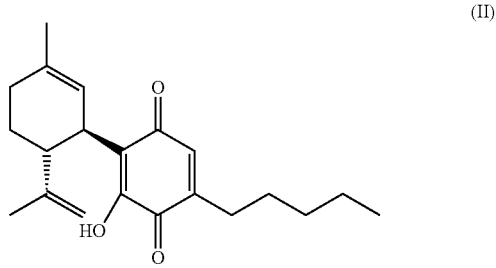

In a preferred embodiment the compounds of the invention are those of Formula (III), (IV), (V) and (VI):

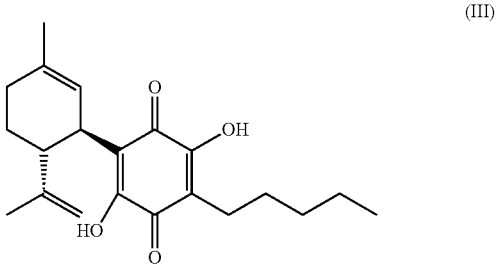

Hydroxy-CBD-Q (H-CBD-Q)

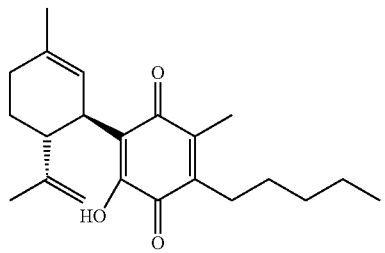

Methyl-CBD-Q (M-CBD-Q)

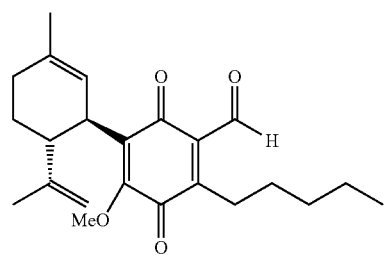

Formyl-Methoxy-CBD-Q (FM-CBD-Q)

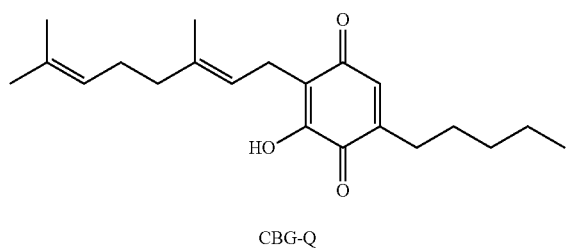

CBG-Q

The second embodiment of the present invention refers to the use of compounds of Formula (I) as medicaments, particularly as PPARg agonists in the treatment of PPARg-related diseases selected from inflammatory diseases (for example: atherosclerosis, inflammatory bowel diseases, rheumatoid arthritis, liver fibrosis, nephropathy, psoriasis, skin wound healing, skin regeneration, pancreatitis, gastritis, neurodegenerative disorders or cancer), metabolic diseases (for example: hypertension, hypertrigliceridemia, hypercholesterolemia (HDL-C), obesity) and Type II diabetes.

The third embodiment of the present invention refers to the use of the above mentioned compounds of Formula (I) for the manufacture of a composition for treating PPARg-related diseases selected from inflammatory diseases (for example: atherosclerosis, inflammatory bowel diseases, rheumatoid arthritis, liver fibrosis, nephropathy, psoriasis, skin wound healing, skin regeneration, pancreatitis, gastritis, neurodegenerative disorders or cancer), metabolic diseases (for example: hypertension, hypertrigliceridemia, hypercholesterolemia (HDL-C), obesity) or Type II diabetes.

The fourth embodiment of the present invention refers to a composition comprising at least one of the above compounds and any suitable acceptable excipient.

The last embodiment of the present invention refers to a method for treating PPARg-related diseases selected from inflammatory diseases (for example: atherosclerosis, inflammatory bowel diseases, rheumatoid arthritis, liver fibrosis, nephropathy, psoriasis, skin wound healing, skin regeneration, pancreatitis, gastritis, neurodegenerative disorders or cancer), metabolic diseases (for example: hypertension, hypertrigliceridemia, hypercholesterolemia (HDL-C), obesity) Type II diabetes; that comprises the administration to the patient of an effective amount of the above composition.

BRIEF DESCRIPTION OF THE FIGURES

The figures of the invention are briefly described below. An in deep explanation of each figure is included in every pertinent example.

The concentration of the tested compound (μM) is shown at the x-axis and the percentage of reduction of fluorescent polarization taken as measurement of binding to PPARg is shown at the y-axis. This figure shows how some cannabinoids comprised in the state of the art binds directly to PPARg, the better values being observed with CBD-Q and CBN.

Figure 2:
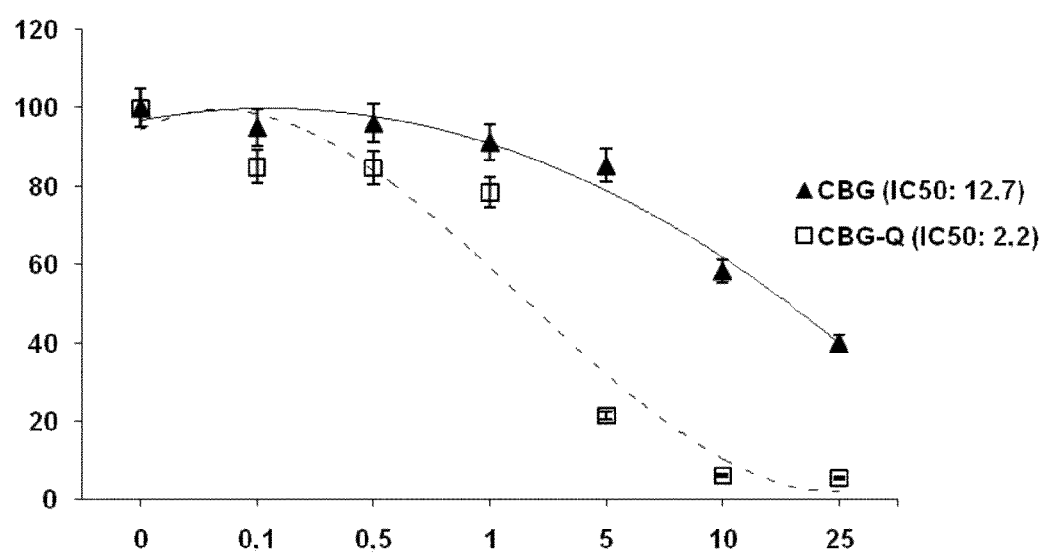

FIG. 2. Comparative PPARg binding assay of CBG vs CBG-Q.

The concentration of the tested compound (μM) is shown at the x-axis and the percentage of reduction of fluorescent polarization taken as measurement of binding to PPARg is shown at the y-axis. This figure indicates that CBG-Q binds directly to PPARg, with the better $IC_{50}$ value, as compared with CBG and also with the best known compounds shown in FIG. 1 (CBD-Q and CBN). Data are given as means with deviation standard error bars of three replicates.

FIG. 3. Transactivation assay.

The concentration of the tested compound (μM) is shown at the x-axis and the PPARg activation fold is shown at the y-axis. This figure shows the effect of CBD and CBD-Q (FIG. 3A) or CBG and CBG-Q (FIG. 3B) on PPARg activity, ratifying CBG-Q as being able to induce PPARg activation with higher efficiency than CBG, CBD and CBD-Q.

Figure 4:
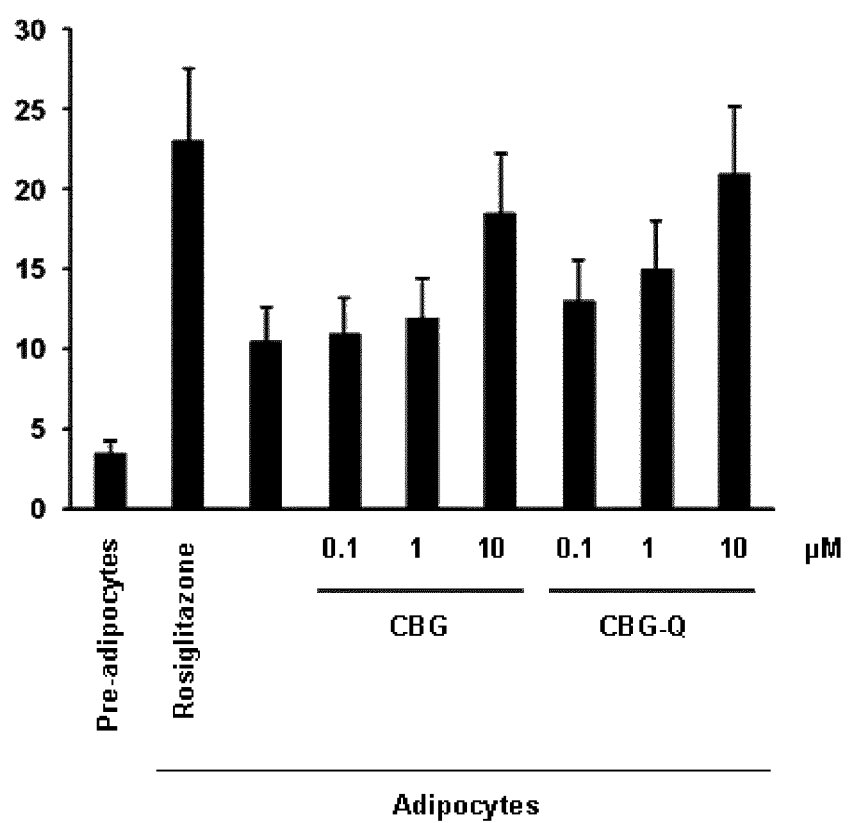

FIG. 4. Adipocyte differentiation assay.

Total triglyceride quantification (mmol/L of 3T3-L1, y-axis) in fully differentiated adipocytes. Data are given as means with deviation standard error bars of three replicates. At all concentrations tested, CBG-Q derivate was found to stimulate the differentiation of fibroblasts to adipocytes. This figure shows the ability to stimulate fat cell differentiation in 3T3 L1 fibroblasts as additional confirmation that CBG-Q is a PPARg ligand. CBG-Q was found to stimulate the differentiation of fibroblasts to adipocytes in a stronger way than CBG. Taken together, these data show for the first time that CBG-Q is a PPARg ligand capable of binding to and increasing its transcriptional activity.

Figure 5:
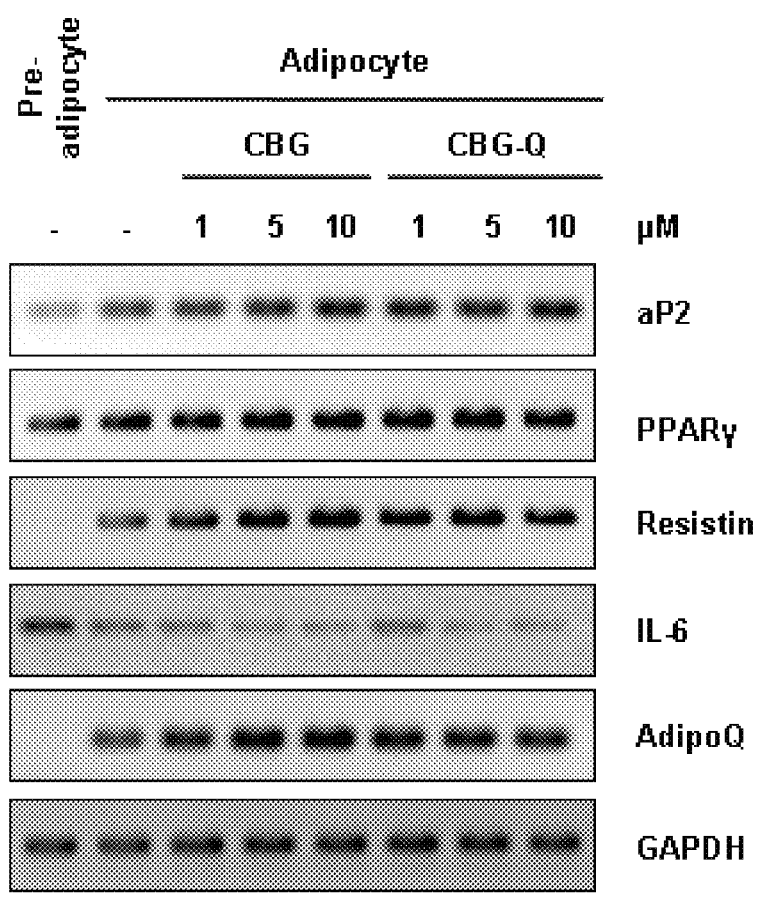

FIG. 5. Comparative effect of CBG and CBG-Q as anti-inflammatory compounds on adipose tissue.

This figure shows the effect of CBG and CBG-Q on the expression of several genes used as markers of adipocyte differentiation (aP2 and PPARg), as well as on several genes that codifies adipokines (Resistin, IL-6, AdipoQ). It was observed a reduction of the pro-inflammatory cytokine IL-6 gene expression, as well as an increment on AdipoQ gene expression, which is the main anti-inflammatory adipokine. The result shows that CBG and CBG-Q have positive effect as anti-inflammatory compounds on adipose tissue.

Figure 6:
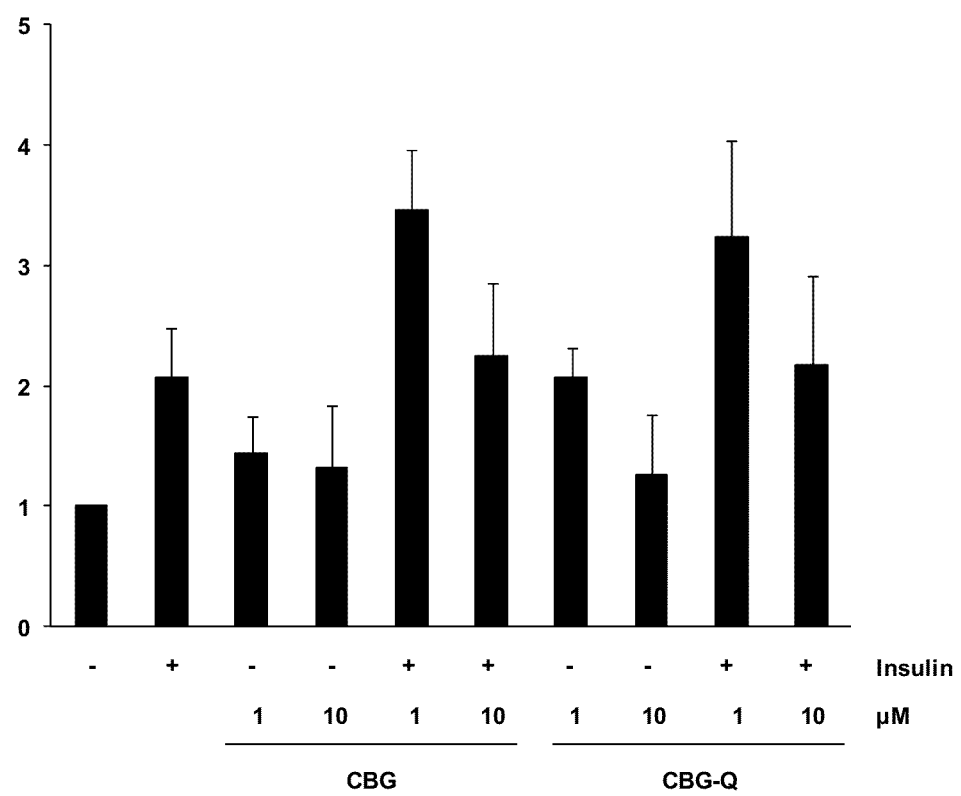

FIG. 6. Comparative effect of CBG and CBG-Q on glucose uptake in 3T3-L1 pre-adipocytes.

This figure shows that both compounds CBG and CBG-Q are able to increment the glucose uptake both in presence (+) and absence (−) of insulin, with CBG-Q showing higher effect than CBG in absence of insulin. The y-axis represents DPM μg protein fold. Thus, CBG-Q can be used to treat insulin resistance through reducing pro-inflammatory adipose tissue conditions and also through incrementing the glucose uptake.

FIG. 7. CBG-Q as PPAR agonist in bone-marrow derived mesenchimal cells. CBG-Q does not inhibit osteoblast differentiation.

Figure 7A:
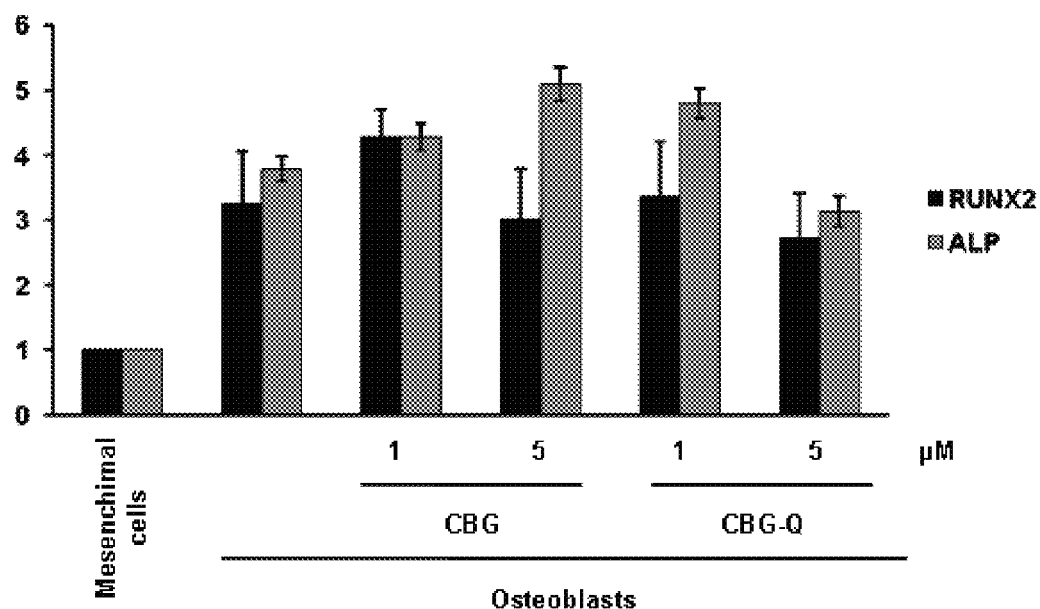

This figure shows the effect of CBG and CBG-Q on specific adipocyte gene expression (PPARg2 isoform and LPL) (FIG. 7B) and specific osteoblast gene expression (RUNX2 and ALP) (FIG. 7A). The gene expression fold is illustrated at the y-axis. It is known that an increase in PPARg activity due to treatment with the antidiabetic thiazolidinedione (TZD) drug rosiglitazone results in a decreased number of osteoblasts and an increased number of adipocytes. However this figure shows that no significant alteration in expression of marker genes both in adipocytes (PPAR and LPL) and osteoblast (Runx2 and LPL) was produced as a consequence of the use of CBG-Q. This result indicates that CBG-Q could be used as PPARg agonist without additional effect on osteoporosis development.

FIG. 8. Effect of several CBD-Q derivates on PPARg activity.

Figure 8A:
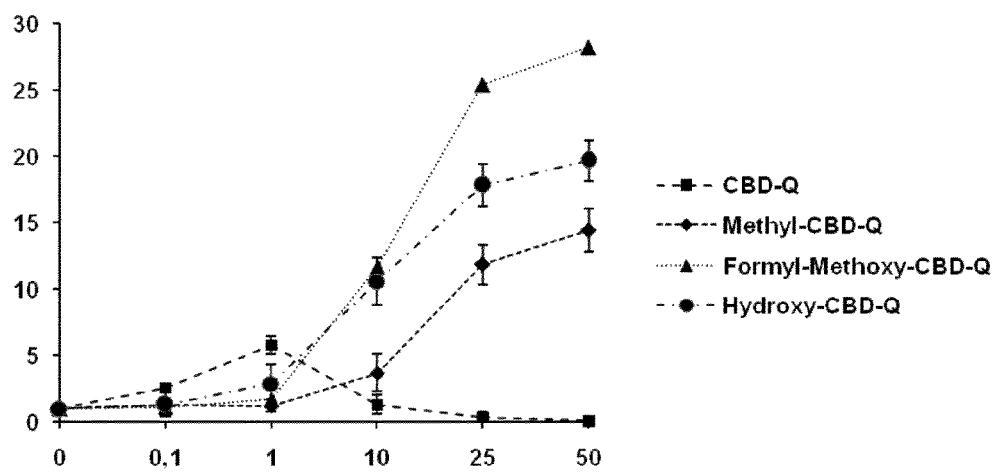

FIG. 8A. The concentration of the tested compound (µM) is shown at the x-axis and the PPARg activation fold is shown at the y-axis. Data are given as means with deviation standard error bars of three replicates. A significant increase in luciferase activity was seen with CBD-Q derivates compared to CBD-Q. This result indicates that CBD-Q derivates are able to induce the PPARg activation with higher efficiency than CBD-Q. FM-CBD-Q showed the highest PPARg activation values.

Figure 8B:
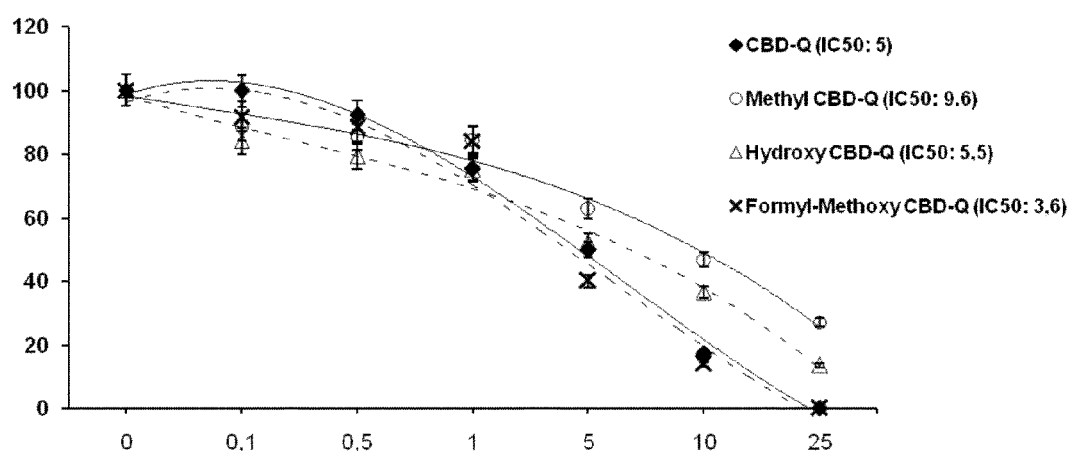

FIG. 8B. The concentration of the tested compound (µM) is shown at the x-axis and the percentage of reduction of fluorescent polarization taken as measurement of PPARg activity in the presence of ligands is shown at the y-axis. $IC_{50}$ are included in legends. Data are given as means with deviation standard error bars of three replicates. This figure indicates that the chemical modifications of CBD-Q maintained or even increased (FM-CBD-Q) the PPARg affinity.

FIG. 8C. Total triglyceride quantification (mmol/L of 3T3-L1, y-axis) in fully differentiated adipocytes. Data are given as means with deviation standard error bars of three replicates. At all concentrations tested, CBD-Q derivates were found to stimulate the differentiation of fibroblasts to adipocytes in a stronger way than CBD and CBD-Q, and without the cytotoxic effect observed for CBD-Q at concentration higher than 1 µM (note the lacking bar). Again, FM-CBD-Q showed the strongest efficiency.

Figure 9:
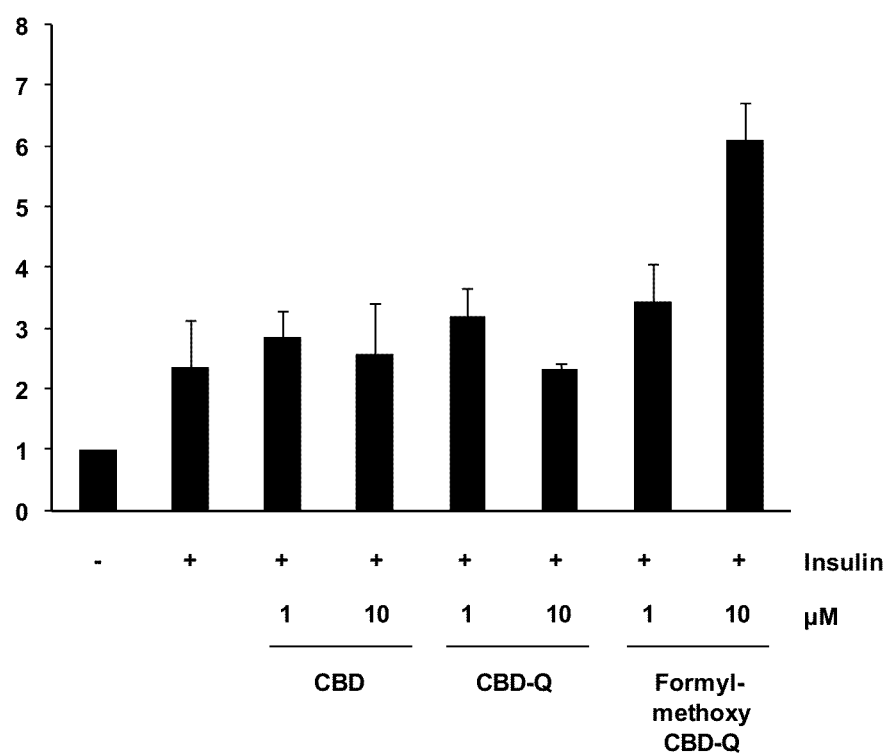

FIG. 9. Comparative effect of CBD, CBD-Q and FM-CBD-Q on glucose uptake in 3T3-L1 pre-adipocytes.

Two doses (1 and 10 µM) were tested in presence of insulin (1.74 µM). Data are given as means with deviation standard error bars of three replicates. The y-axis represents DPM µg protein fold. The results show that the compound FM-CBD-Q is able to increase the glucose uptake also in presence of insulin.

EXAMPLES

The examples of the present invention described below aim to illustrate its preferred embodiments without limiting its scope of protection.

Example 1

PPARg Binding Assay

Figure 1:
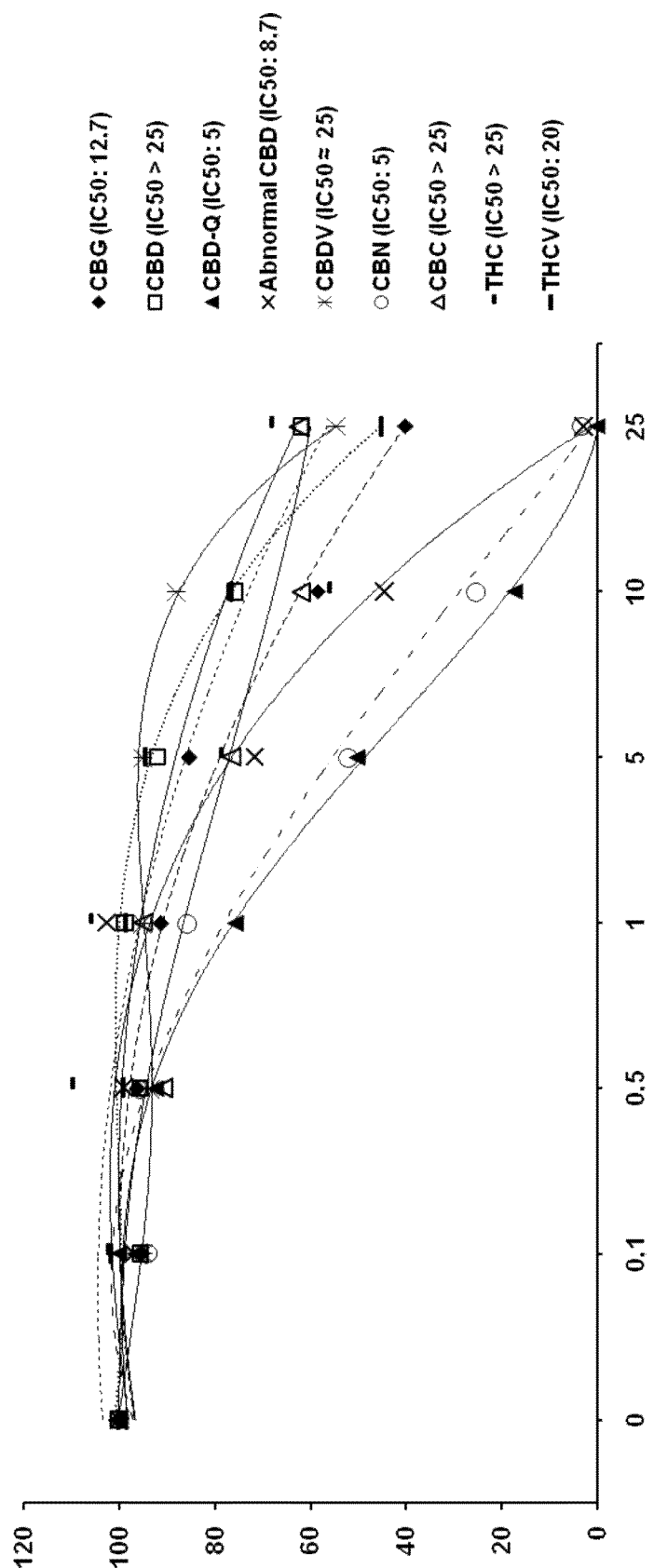
FIG. 1. PPARg binding assay of some known cannabinoids.

The capacity of the compounds of the invention of binding to the PPARg-ligand binding domain was measured using the PolarScreen™ PPARg Competitor Assay Green kit (Invitrogen). Briefly, the competitors were diluted in reaction buffer in a black 384 shallow well plate (NUNC). The purified PPARg-ligand binding domain and fluorescent PPARg ligand (Fluormone™ PPAR Green) were then added. Samples were incubated at room temperature for 2 h and fluorescence polarization obtained by reading the plate using a Tecan Genius Pro with an excitation wavelength of 485 nm and emission wavelength of 535 nm. As shown in FIG. 1, this PPARg binding assay was initially carried out with cannabinoid comprised in the state of the art, showing also their $IC_{50}$ value: CBG (cannabigerol), CBD (cannabidiol), CBDV (cannabidivarine), CBN (cannabinol), CBC (cannabicrhromen), THC (Δ8-tetrahydrocannbinol), THCV (Δ8-tetrahydrocannbinol-viridine) CBD-Q (CBD-Quinone) and Abnormal-CBD. Data are given as means with deviation standard error bars of three replicates. Those cannabinoids displaced the fluorescent Fluormone™ PPAR Green ligand from the PPAR-LBD/Fluormone™ PPAR Green complex, resulting in a reduction of polarisation value. This result indicates that said cannabinoids binds directly to PPARg, the better values being observed with CBD-Q and CBN. Moreover, FIG. 2 illustrates the same PPARg binding assay but carried out with the cannabinoid CBG comprised in the state of the art and the cannabinoid CBG-Q of the invention, showing also their $IC_{50}$ values. Data are given as means with deviation standard error bars of three replicates. CBG-Q displaced the fluorescent Fluormone™ PPAR Green ligand from the PPAR-LBD/Fluormone™ PPAR Green complex with better $IC_{50}$ than any of the other cannabinoids. This result indicates that CBG-Q binds directly to PPARg, with the best $IC_{50}$ value, compared with CBG (FIG. 2) and also with CBD-Q and CBN (FIG. 1).

Example 2

Cell Lines Used in the Invention

Several cell lines were used in the present invention: AGS, human gastric adenocarcinome; HCT116, human colon carcinoma; HeLa, human cervical carcinoma; MDA, human breast cancer; T47D, human breast adenocarcinoma; 293T, human renal epithelial cell line; and 3T3-L1, mouse embryonic fibroblast adipose-like. All cellular lines were grown at 37° C. and 5% $CO_2$ in supplemented Dulbecco's modified Eagle's medium (DMEM) (Cambrex Co., Barcelona, Spain), containing 10% heat-inactivated fetal bovine serum (FBS) (Cambrex Co., Barcelona, Spain), 2 mM glutamine, penicillin (50 U/ml) and streptomycin (50 mg/ml). Mesenchimal cells (MSC) were obtained from donors through the Hematology. Service at the Reina Sofia University Hospital (Cordoba, Spain). MSC were maintained in α-MEM with 15% FBS.

Example 3

3T3-L1 Adipocyte Differentiation Assay

The 3T3-L1 preadipocyte cell line was plated at a concentration of $2 \times 10^5$ cell/well in 6-well plates for RNA isolations and tygliceride cunatification. 3T3-L1 fibroblasts were grown until confluence (3 days) in DMEM with 10% FBS and antibiotics. Then (day 0), medium was supplemented with 1 µM dexamethasone, IBMX 0.5 mM and 10 µg/ml insulin, to induce differentiation for 2 days. In day 2, the medium was supplemented only with 5 µg/ml insulin for two more days. All mediums used were additionally supplemented with cannabinoids, or rosiglitazone (1 µM) as control, since day 0. In case of RNA extractions, cells were harvested on day 4. For trygliceride cuantification, cells were maintained in medium supplemented with cannabinoids until day 12 and refreshed every two days. This example is illustrated by FIG. 4 which shows the effect of CBG and CBG-Q on 3T3-L1 cells adipogenesis. As cited above rosiglitazone (1 µM) was used as control of adipocyte differentiation. The ability to stimulate fat cell differentiation in 3T3 L1 fibroblasts was evaluated in order to confirm that CBG-Q is a PPARg ligand. CBG-Q was found to stimulate the differentiation of fibroblasts to adipocytes in a stronger way than CBG. It is shown by the tryglicéride accumulation in adipocytes. Taken together, these data show for the first time that CBG-Q is a PPARg ligand capable of binding to and increasing the transcriptional activity of PPARg.

Example 4

Effect of CBG and CBG-Q on Specific Adipocyte Gene Expression (aP2 and PPARg), and Adipokines Gene Expression (Resistin, IL-6, AdipoQ)

The effect of CBG and CBG-Q on several genes used as markers of adipocyte differentiation (aP2 and PPARγ), as well as on several genes that codifies adipokines (Resistin, IL-6, AdipoQ), was examined by use of the PCR. GAPDH gene was used as houskeeping gene. CBG and CBG-Q showed additive gene expression response compared to adipocyte without any compound added, confirming their stimulating effect on adipocyte differentiation. It was observed a reduction of the pro-inflammatory cytokine IL-6, as well as an increment on AdipoQ, which is the main anti-inflammatory adipokine. The result shows that CBG and CBG-Q have positive effect as anti-inflammatory compounds on adipose tissue. The production of pro-inflammatory cytokines and the reduction of AdipoQ in adipose tissue leads to an increment of insulin resistance not only on adipose tissue, but also on muscle and liver, what conduces to type II diabetes at short term (FIG. 5).

Example 5

Glucose Uptake

For assays of 2-deoxy-D-glucose transport 3T3-L1 pre-adipocytes cultured in 12-well plates were deprived of serum by incubation for 2 hours. The cells were then incubated with 1.74 µM insulin for 20 minutes in 450 µl of KRH buffer (25 mM HEPES-NaOH [pH 7.4], 120 mM NaCl, 5 mM KCl, 1.2 mM $MgSO_4$, 1.3 mM $CaCl_2$, and 1.3 mM $KH_2PO_4$). Glucose transport was initiated by the addition of 50 µl of KRH buffer containing 0.5 mM 2-deoxy-D-[1, 2-3H]glucose (0.25 µCi) to each well; after 5 minutes, transport was terminated by washing the cells 3 times with ice-cold KRH buffer. The cells were solubilized, and the incorporated radioactivity was measured by liquid scintillation counting. This assay is illustrated by FIG. 6 which shows the analysis of the effect of CBG and CBG-Q on glucose uptake in 3T3-L1 pre-adipocyte. Two doses were tested in presence and absence of insulin (1.74 µM).

Data are given as means with deviation standard error bars of three replicates. The results show that both compounds are able to increment the glucose uptake both in presence and absence of insulin, with CBG-Q showing a higher effect than CBG in absence of insulin. Thus, CBG-Q could be used to treat insulin resistance through reducing pro-inflammatory adipose tissue conditions and also through incrementing the glucose uptake. Also FIG. 9 shows the effect of CBD, CBD-Q and FM-CBD-Q on glucose uptake in 3T3-L1 pre-adipocytes. Two doses were tested in presence of insulin (1.74 µM). Data are given as means with deviation standard error bars of three replicates. To analyse the effect of FM-CBD-Q on glucose uptake in 3T3-L1 pre-adipocyte, two doses were tested in presence of insulin. The results show that the compound FM-CBD-Q is able to increment the glucose uptake in presence of insulin.

Example 6

Figure 7B:
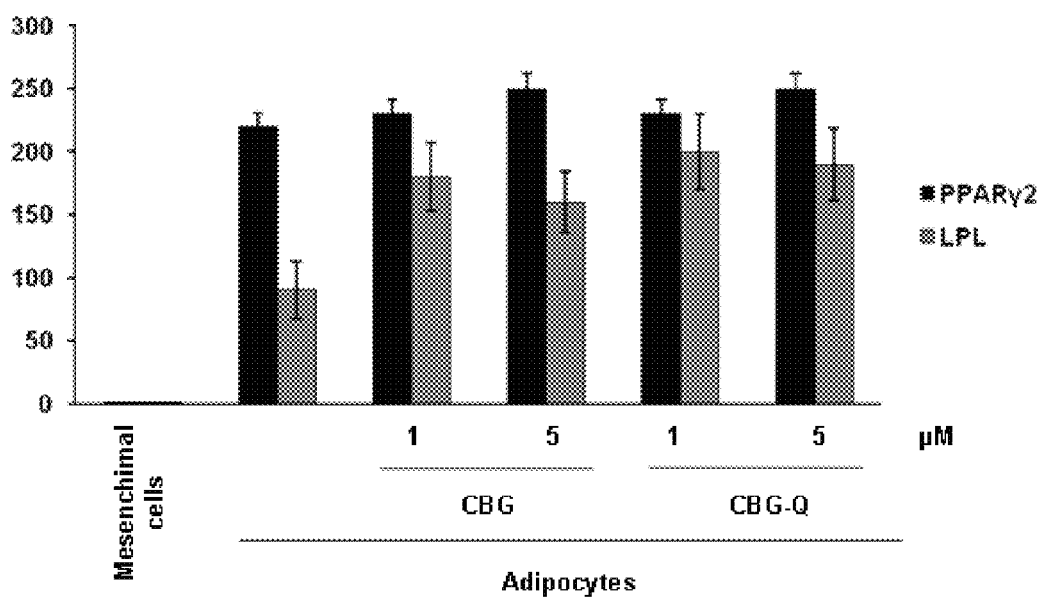

CBG-Q as PPAR Agonist in Bone-marrow Derived Mesenchimal Cells. CBG-Q does not Inhibit Osteoblast Differentiation Cells were plated at 500 cell/$cm^2$ on P6 plates (TPP, Trasadingen, Switzerland) containing α-MEM medium with 10% FBS. When the cell cultures were 80-90% confluent, the medium was supplemented with $10^{-8}$ M dexamethasone, 0.2 mM ascorbic acid and 10 mM β-glycerolphosphate to induce differentiation to osteoblasts, and $5\times10^{-7}$ M dexamethasone, 0.5 mM isobutylmethylxanthine and 50 mM indometacin to induce differentiation to adipocytes. All inducers were from Sigma-Aldrich. MSC (mesenchymal stem cells) were grown in an osteogenic or adipogenic medium for 21 days, together with a corresponding control (in the absence of differentiation inducers). Cell samples were collected at day 13. As shown in FIG. 7 the effect of CBG and CBG-Q on specific adipocyte gene expression (PPARg2 and LPL) (FIG. 7B) and specific osteoblast gene expression (Runx2 and ALP) (FIG. 7A) was evaluated. Expression values of nuclear ribosomal DNA were used to normalise the obtained values. Adipocyte and osteoblasts were obtained by differentiation of human mesenchymal stem cells grown in adipogenic or osteoblastogenic specific differentiation culture mediums. Analysis was performed by QRT-PCR, and results are presented as means with deviation standard error bars of three replicates. Bone forming osteoblasts and fat forming adipocytes are both derived from mesenchymal stem cells (MSCs). An increase in PPARg activity due to treatment with the antidiabetic thiazolidinedione (TZD) drug rosiglitazone results in a decreased number of osteoblasts and an increased number of adipocytes. To test the effect of CBG and CBG-Q on MSC differentiation to osteoblast or adipocytes, the compounds were added to differentiation medium for 21 days and specific gene expression was measured by quantitative real-time PCR. It was observed no significant alteration in expression of marker genes both in adipocytes (PPAR and LPL) and osteoblast (Runx2 and LPL). This result indicates that CBG-Q could be used as PPAR agonist without additional effect on osteoporosis development.

Example 7

Cytotoxicity MTT 3-(4,5-Dimethylthiazol-2-yl)-2,5-diphenyltetrazolium bromide) Test Aliquots of cell suspensions were dispensed at 100 µl volumes into wells of 96-well tissue culture plates at a density of $10^4$ cells/well. Various concentrations of cannabinoids were added, and their efficacy was tested after 24 hours with the use of the MTT assay (Carmichael et al., 1987). In each MTT assay, every concentration of the assayed substance was tested in three replicates. The inhibitory effect of the various compounds was calculated as percentage inhibition relative to cells treated with vehicle (0.5% DMSO).

Table 2 shows IC$_{50}$ values of MTT (3-(4,5-Dimethylthiazol-2-yl)-2,5-diphenyltetrazolium bromide) cytotoxicity assay in several cellular lines after 24 hours of treatment with CBD, CBD-Q, CBG and CBG-Q. In a MTT (3-(4,5-Dimethylthiazol-2-yl)-2,5-diphenyltetrazolium bromide, a tetrazole) cytotoxicity assay (24 hours of treatment) in several cellular lines, CBG-Q showed similar cytotoxic effect compared to CBG and reduced values compared to CBD and CBD-Q. The strongest cytotoxic effect was observed with CBD-Q. Cellular lines are derived from: AGS, human gastric adenocarcinome; HCT116, human colon carcinoma; HeLa, human cervical carcinoma; MDA, human breast cancer; T47D, human breast adenocarcinoma; 3T3-L1, mouse embryonic fibroblast-adipose like.

TABLE 2

| Cell line | COMPOUND | | | |
|---|---|---|---|---|
| | CBD | CBD-Q | CBG | CBG-Q |
| AGS | 25.0 | 7.44 | >50.0 | 48.0 |
| HCT116 | >50.0 | 9.8 | >50.0 | 47.0 |
| HeLa | >50.0 | 40.5 | >50.0 | >50.0 |
| MDA | >50.0 | 10.1 | >50.0 | 49.0 |
| T47D | 35.0 | 20.0 | 47.0 | 44.0 |
| 3T3-L1 | 30.0 | 12.0 | 42.2 | 49.0 |

Table 3 shows IC$_{50}$ values of MTT (3-(4,5-Dimethylthiazol-2-yl)-2,5-diphenyltetrazolium bromide, a tetrazole) cytotoxicity assay in several cellular lines after 24 hours of treatment with CBD-Q derivates. In a MTT (3-(4,5-Dimethylthiazol-2-yl)-2,5-diphenyltetrazolium bromide) cytotoxicity assay (24 hours of treatment) in several cellular lines, all CBD-Q derivates showed reduced cytotoxic effect compared to CBD-Q. Cellular lines are derived from: AGS, human gastric adenocarcinome; HCT116, human colon carcinoma; HeLa, human cervical carcinoma; MDA, human breast cancer; T47D, human breast adenocarcinoma; 3T3-L1, mouse embryonic fibroblast-adipose like.

TABLE 3

| Cell line | COMPOUND | | | |
|---|---|---|---|---|
| | CBD-Q | Hydroxy CBD-Q | Formyl-Methoxy CBD-Q | Methyl CBD-Q |
| AGS | 7.44 | >50.0 | >50.0 | >50.0 |
| HCT116 | 9.8 | >50.0 | >50.0 | >50.0 |
| HeLa | 40.5 | >50.0 | >50.0 | >50.0 |
| MDA | 10.1 | >50.0 | >50.0 | >50.0 |
| T47D | 17.1 | >50.0 | >50.0 | >50.0 |
| 3T3-L1 | 12.0 | >50.0 | >50.0 | >50.0 |

Example 8

Figure 3A:
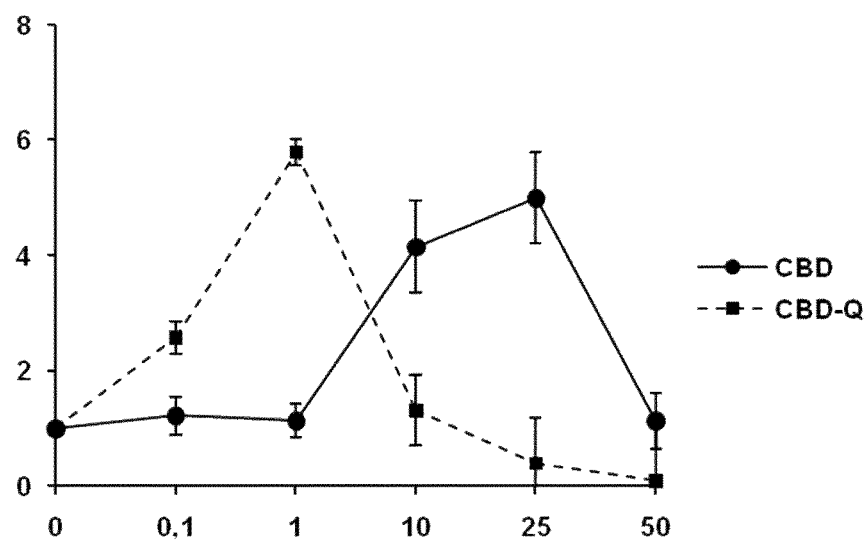
Figure 3B:
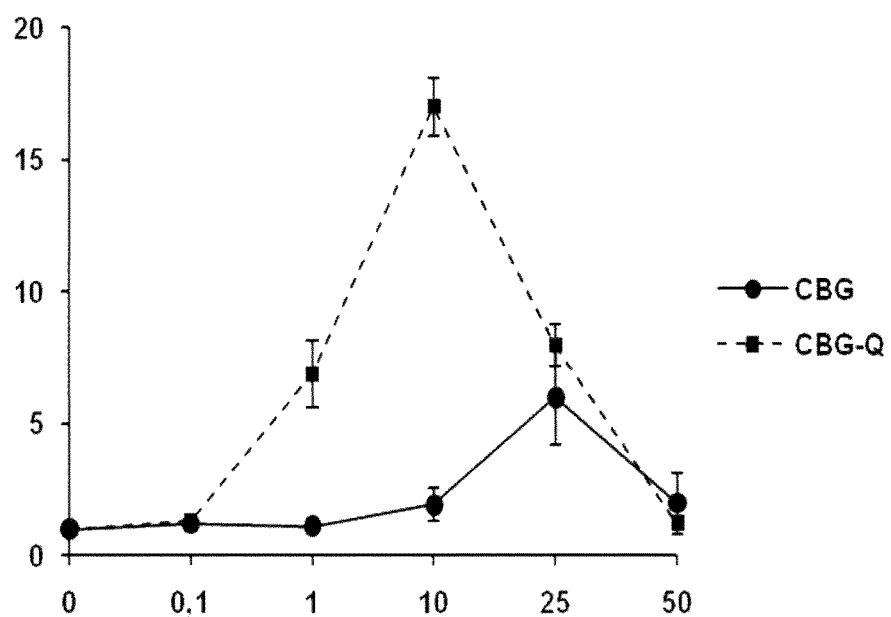

Transient Transfections and Luciferase Assays $7 \times 10^3$ 293T cells were seeded in BD Falcon™ White with Clear Bottom 96-well Microtest™ Optilux™ Plate for 24 hours. Afterwards, cells were transfected with the indicated plasmids using Rottifect reactives (ROTH, Karlsruhe, Germany) according to the manufacturer's recommendations. 24 h postransfection, cells were pretreated with increasing doses of cannabinoids for 6 hours. Then, the cells were lysed in 25 mM Tris-phosphate pH 7.8, 8 mM MgCl$_2$, 1 mM DTT, 1% Triton X-100, and 7% glycerol. Luciferase activity was measured in the cell lysate using a TriStar LB 941 multimode microplate reader (Berthold) and following the instructions of the Luciferase Assay Kit (Promega, Madison, Wis., USA). Protein concentration was measured by the Bradford assay (Bio-Rad, Richmond, Calif., USA). The background obtained with the lysis buffer was subtracted in each experimental value and the specific transactivation expressed as a fold induction over untreated cells. All the experiments were repeated at least three times. Plasmid used were Gal4-hPPARgamma (plasmid name: pCMV-BD-hPPARg, made in Sinal Laboratory, Dept. of Pharmacology, Dalhousie University) and Gal4 luc reporter plasmid that includes five Gal4 DNA binding sites fused to the luciferase gene. The above assay is illustrated by FIG. 3 which shows the effect of CBD and CBD-Q (FIG. 3A) or CBG and CBG-Q (FIG. 3B), on PPARg activity, by means of a transactivation assay performed in 293T cells transiently overexpressing PPARg in combination with a luciferase reporter gene (PPARg-GAL4/GAL4-LUC) and treated with cannabinoids for 6 hours. Data are given as means with deviation standard error bars of three replicates. A significant increase in luciferase activity was seen with quinone derivates as compared with untreated cells. This result confirms that the compound CBG-Q is able to induce the PPARg activation with higher efficiency than CBG Moreover FIG. 8A shows a transactivation assay performed in 293T cells transiently overexpressing PPARg in combination with a luciferase reporter gene (PPARg-GAL4/GAL4-LUC) and treated with cannabinoids for 6 hours. Data are given as means with deviation standard error bars of three replicates. Compared with untreated cells (indicated with value 1 as reference), a significant increase in luciferase activity was seen with CBD-Q derivates compared to CBD-Q. This result indicates that CBD-Q derivates are able to induce the PPARg activation with higher efficiency than CBD-Q. FM-CBD-Q showed the highest PPARg activation values. Also FIG. 8B illustrates a PPARg binding assay demonstrating that CBD-Q derivates displaced the fluorescent Fluormone™ PPAR Green ligand from the PPAR-LBD/Fluormone™ PPAR Green complex, resulting in a reduction of polarisation value. This result indicates that the chemical modifications of CBD-Q maintained or even incremented (FM-CBD-Q) the PPARg affinity.

Example 9

Total Triglyceride Quantification

3T3-L1 fully differentiated adipocytes were washed in PBS and sonicated three times for 5 seconds in a buffer containing 2 M NaCl, 2 mM EDTA and 50 mM sodium phosphate pH 7.4 to release cellular content. Total triglyceride content released was quantified using a commercial Triglyceride Assay kit (Applied BioSystem, Spain) based on a colorimetric reaction and measured by absorbance at 500 nm in a spectrophotometer. FIG. 8C confirms that CBD-Q derivates are PPARg ligands in culture cells, by examining the ability to stimulate fat cell differentiation in 3T3 L1 fibroblasts. At all concentrations tested, CBD-Q derivates were found to stimulate the differentiation of fibroblasts to adipocytes in a stronger way than CBD and CBD-Q, and without the cytotoxic effect observed for CBD-Q at concentration higher than 1 μM (note lacking bar).

Example 10

PCR and Real-Time Quantitative PCR Used in the Invention (Examples 4 and 6)

The PCR reaction consisted of 25 μl of a mixture containing: 1×PCR buffer, 1.5 mM MgCl$_2$, 0.2 mM dNTPs, 0.2 μM of each sequence-specific primers, 1 µl of transcribed cDNA, and 0.5 U of Taq polymerase (Biotools). For QRT-PCR it was used a Bio-Rad iCycler iQ Real Time PCR instrument and iQ SYBR™ Green Supermix (Bio-Rad, Richmond, Calif., USA). Amplification was performed in a final volume of 50 µl with 1 µl of cDNA, 25 µl of 2×SYBR Green Supermix (100 mM KCl, 40 mM Tris-HCl pH 8.4, dNTP 0.4 mM each, 50 u/ml iTaq polimerase, 6 mM $MgCl_2$, SYBR Green I, and 20 nM fluorescein) and 2 µl of primers 2 µM. The specific primer sequences are shown in Table 4. The thermal cycling conditions were: 94° C. for 2 min, followed by 35 cycles of 94° C. for 15 s, 60° C. for 30 s, and 72° C. for 1 min. A final step of extension at 72° C. for 5 min was also included. To assess the correct amplification a melting program was also included [70° C., 10 s (+0.5° C.×60)]. Amplified products were additionally analyzed by electrophoresis in 1.8% agarose gel containing 0.5 ug/ml ethidium bromide. Relative expression values were calculated according to Pedersen (2001).

TABLE 4

Oligonucleotide PCR primer sequences.

| | |
|---|---|
| PPARg-Up | SEQ ID NO: 1 |
| PPARg-Low | SEQ ID NO: 2 |
| Adiponectin-Up | SEQ ID NO: 3 |
| Adiponectin-Low | SEQ ID NO: 4 |
| IL-6-Up | SEQ ID NO: 5 |
| IL-6-Low | SEQ ID NO: 6 |
| Resistin-Up | SEQ ID NO: 7 |
| Resistin-Low | SEQ ID NO: 8 |
| aP2-Up | SEQ ID NO: 9 |
| aP2-Low | SEQ ID NO: 10 |
| GAPDH-Up | SEQ ID NO: 11 |
| GAPDH-Low | SEQ ID NO: 12 |
| Nuclear ribosomal DNA (rRNA)-Up | SEQ ID NO: 13 |
| Nuclear ribosomal DNA (rRNA)-Low | SEQ ID NO: 14 |
| Alkaline phosphatase (alp)-Up | SEQ ID NO: 15 |
| Alkaline phosphatase (alp)-Low | SEQ ID NO: 16 |
| Runt-related transcription factor 2 (runx2)-Up | SEQ ID NO: 17 |
| Runt-related transcription factor 2 (runx2)-Low | SEQ ID NO: 18 |
| PPAR-g2-Up | SEQ ID NO: 19 |
| PPAR-g2-Low | SEQ ID NO: 20 |
| Lipoprotein lipase (lpl)-Up | SEQ ID NO: 21 |
| Lipoprotein lipase (lpl)-Low | SEQ ID NO: 22 |

Example 11

Oxidation of CBG to CBG Hydroxyquinone (CBG-Q)

To a cooled (ice bath) solution of CBG (200 mg, 0.64 mmol) in HMPA (5 mL), nBuLi in hexane (0.66 mL, 2.5 M, 1.65 mmol, 2.5 mol. equiv.) was added dropwise. The addition was done under normal aerobic condition. The cooling bath was then removed and the solution was heated at 50° C. (oil bath). The reaction was monitored by TLC (petroleum ether-EtOAc 9:1, Rf. CBG=0.32; Rf CBGquinone=0.46) and, after two hours, was worked up by the addition of 2N H2SO4 and extraction with EtOAc. The organic phase was dried (Na2SO4), evaporated and purified by gravity column chromatography (petroleum ether-EtOAc 95:5 as eluant), affording 130 mg (62%) of CBG-hydroxyquinone.

REFERENCES

Bernardo, A., Minghetti, L., 2008. Regulation of Glial Cell Functions by PPAR-gamma natural and Synthetic Agonists. PPAR Res. 2008, 864140.

Bishop-Bailey, D., 2000. Peroxisome proliferator-activated receptors in the cardiovascular system. Br. J. Pharmacol. 129, 823-831, Bouaboula M, Hilairet S, Marchand J, Fajas L, Le Fur G, Casellas P (2005). Anandamide induced PPARgamma transcriptional activation and 3T3-L1 preadipocyte differentiation. Eur J Pharmacol 517:174-181.

Burstein S. PPAR-gamma: a nuclear receptor with affinity for cannabinoids. Life Sci. 2005 Aug. 19; 77(14):1674-84.

Delerive P, Fruchart J C, Staels B, 2001. Peroxisome proliferator-activated receptors in inflammation control. J. Endocrinol. 169, 453-459.

Fievet C, Fruchart J C, Staels B, 2006. PPAR alpha and PPAR gamma dual agonists for the treatment of type2 diabetes and the metabolicsyndrome. Curr. Opin. Pharmacol. 6, 606-614.

Fu J, Gaetani S, Oveisi F, Lo Verme J, Serrano A, Rodriguez De Fonseca F et al. (2003). Oleylethanolamide regulates feeding and body weight through activation of the nuclear receptor PPAR-alpha. Nature 425: 90-93

Gelman, L., Feige, J. N., Desvergne, R, 2007. Molecular basis of selective PPARgamma modulation for the treatment of type 2 diabetes. Biochim. Biophys. Acta 1771, 1094-1107.

Hsueh, W. A., Bruemmer, D., 2004. Peroxisome proliferator-activated receptor gamma: implications for cardiovascular disease. Hypertension 43, 297-305.

Lehmann J M, Moore L B, Smith-Oliver T A, Wilkison W O, Willson T M, Kliewer S A. An antidiabetic thiazolidinedione is a high affinity ligand for peroxisome proliferator-activated receptor gamma (PPAR gamma) J Biol. Chem. 1995 Jun. 2; 270(22):12953-6.

Liu J, Li H, Burstein S H, Zurier R B, Chen J D, 2003. Activation and binding of peroxisome proliferator-activated receptor gamma by synthetic cannabinoid ajulemic acid. Mol. Pharmacol. 63, 983-992.

Lottenberg S A, Glezer A, Turatti L A. Metabolic syndrome: identifying the risk factors. J Pediatr (Rio J) 2007; 83(5 Suppl):S204-8.

LoVerme J, Russo R, La Rana G, Fu J, Farthing J, Mattace-Raso G et al. (2006). Rapid broad-spectrum analgesia through activation of peroxisome proliferator-activated receptor-alpha. J Pharmacol Exp Ther 319: 1051-1061.

Murphy G J, Holder J C. PPAR-gamma agonists: therapeutic role in diabetes, inflammation and cancer. Trends Pharmacol Sci 2000; 21(12):469-74.

O'Sullivan S E, Kendall D A. Cannabinoid activation of peroxisome proliferator-activated receptors: Potential for modulation of inflammatory disease. Immunobiology. 2009 Oct. 13.

O'Sullivan S E, Sun Y, Bennett A J, Randall M D, Kendall D A. Time-dependent vascular actions of cannabidiol in the rat aorta. Eur J. Pharmacol. 2009 Jun. 10; 612(1-3): 61-8.

O'Sullivan S E. Cannabinoids go nuclear: evidence for activation of peroxisome proliferator-activated receptors. Br J. Pharmacol. 2007 November; 152(5):576-82.

Rosen E D, MacDougald O A. Adipocyte differentiation from the inside out. Nat Rev Mol Cell Biol. 2006 December; 7(12):885-96.

Stienstra R, Duval C, Muller M, Kersten S, 2007. PPARs, obesity, and inflammation. PPAR Res. 2007, 95974.

Sun Y, Bennett A. Cannabinoids: A New Group of Agonists of PPARs. PPAR Res. 2007; 2007:23513.

Széles, L., Töröcsik, D., Nagy, L., 2007. PPARgamma in immunity and inflammation: cell types and diseases. Biochim. Biophys. Acta 1771, 1014-1030.

Tachibana K, Yamasaki D, Ishimoto K, Doi T. The Role of PPARs in Cancer. PPAR Res. 2008; 2008:102737.

Tontonoz P, Spiegelman B M. Fat and beyond: the diverse biology of PPARgamma Annu Rev Biochem. 2008; 77: 289-312. Review.

Vanden Berghe W, Vermeulen L, Delerive P, DeBosscher K Staels B, Haegeman G. 2003. A paradigm for gene regulation: inflammation, NF-kB and PPAR. Adv. Exp. Med. Biol. 544, 181-196.

The invention claimed is:

1. Compound characterized by having the formula (VI):

(VI)

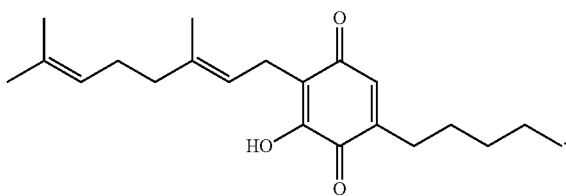

2. A method for treating PPARg-related disease in a patient in need thereof that comprises administration to the patient of an effective amount of a pharmaceutical composition comprising a compound of Formula (VI):

(VI)

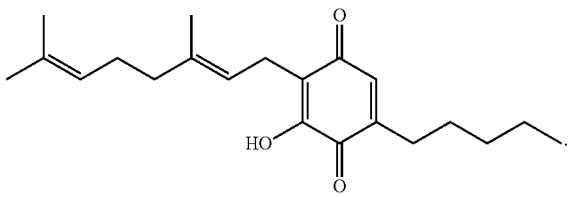

3. The method, according to claim 2, wherein the PPARg-related disease is selected from: inflammatory diseases, metabolic diseases and type II diabetes.

4. The method, according to claim 2, wherein the PPARg-related disease is a metabolic disease selected from: hypertension, hypertrigliceridemia, hypercholesterolemia (HDL-C) or obesity.

5. The method, according to claim 3, wherein the PPARg-related disease is a metabolic disease selected from: hypertension, hypertrigliceridemia, hypercholesterolemia (HDL-C) or obesity.

6. The method, according to claim 2, wherein the PPARg-related disease is an inflammatory disease selected from: atherosclerosis, inflammatory bowel disease, liver fibrosis, nephropathy, psoriasis, skin wound healing, skin regeneration, pancreatitis, or gastritis.

7. The method, according to claim 3, wherein the PPARg-related disease is an inflammatory disease selected from: atherosclerosis, inflammatory bowel disease, liver fibrosis, nephropathy, psoriasis, skin wound healing, skin regeneration, pancreatitis, or gastritis.

8. A Pharmaceutical composition comprising at least the compound of claim 1, and an acceptable excipient or carrier.

* * * * *

SEQUENCE LISTING

```
<160> NUMBER OF SEQ ID NOS: 22

<210> SEQ ID NO 1
<211> LENGTH: 20
<212> TYPE: DNA
<213> ORGANISM: Artificial Sequence
<220> FEATURE:
<223> OTHER INFORMATION: Synthetic Construct

<400> SEQUENCE: 1
ccagagtctg ctgatctgcg                                                   20

<210> SEQ ID NO 2
<211> LENGTH: 20
<212> TYPE: DNA
<213> ORGANISM: Artificial Sequence
<220> FEATURE:
<223> OTHER INFORMATION: Synthetic Construct

<400> SEQUENCE: 2
gccacctctt tgctctgctc                                                   20

<210> SEQ ID NO 3
<211> LENGTH: 20
<212> TYPE: DNA
<213> ORGANISM: Artificial Sequence
<220> FEATURE:
<223> OTHER INFORMATION: Synthetic Construct

<400> SEQUENCE: 3
ggctctgtgc tgctccatct                                                   20

<210> SEQ ID NO 4
<211> LENGTH: 25
<212> TYPE: DNA
<213> ORGANISM: Artificial Sequence
<220> FEATURE:
<223> OTHER INFORMATION: Synthetic Construct

<400> SEQUENCE: 4
agagtcgttg acgttatctg catag                                             25

<210> SEQ ID NO 5
<211> LENGTH: 22
<212> TYPE: DNA
<213> ORGANISM: Artificial Sequence
<220> FEATURE:
<223> OTHER INFORMATION: Synthetic Construct

<400> SEQUENCE: 5
acaaccacgg ccttccctac tt                                                22

<210> SEQ ID NO 6
<211> LENGTH: 23
<212> TYPE: DNA
<213> ORGANISM: Artificial Sequence
<220> FEATURE:
<223> OTHER INFORMATION: Synthetic Construct
```

<400> SEQUENCE: 6
caggatttcc cagcgaacat gtg                                    23

<210> SEQ ID NO 7
<211> LENGTH: 21
<212> TYPE: DNA
<213> ORGANISM: Artificial Sequence
<220> FEATURE:
<223> OTHER INFORMATION: Synthetic Construct

<400> SEQUENCE: 7
gtacccacgg gatgaagaac c                                      21

<210> SEQ ID NO 8
<211> LENGTH: 18
<212> TYPE: DNA
<213> ORGANISM: Artificial Sequence
<220> FEATURE:
<223> OTHER INFORMATION: Synthetic Construct

<400> SEQUENCE: 8
gcagagccac aggagcag                                          18

<210> SEQ ID NO 9
<211> LENGTH: 19
<212> TYPE: DNA
<213> ORGANISM: Artificial Sequence
<220> FEATURE:
<223> OTHER INFORMATION: Synthetic Construct

<400> SEQUENCE: 9
aagtgggagt gggctttgc                                         19

<210> SEQ ID NO 10
<211> LENGTH: 21
<212> TYPE: DNA
<213> ORGANISM: Artificial Sequence
<220> FEATURE:
<223> OTHER INFORMATION: Synthetic Construct

<400> SEQUENCE: 10
tccccattta cgctgatgat c                                      21

<210> SEQ ID NO 11
<211> LENGTH: 22
<212> TYPE: DNA
<213> ORGANISM: Artificial Sequence
<220> FEATURE:
<223> OTHER INFORMATION: Synthetic Construct

<400> SEQUENCE: 11
tggcaaagtg gagattgttg cc                                     22

<210> SEQ ID NO 12
<211> LENGTH: 21
<212> TYPE: DNA
<213> ORGANISM: Artificial Sequence
<220> FEATURE:
<223> OTHER INFORMATION: Synthetic Construct

<400> SEQUENCE: 12
aagatggtga tgggcttccc g                                      21

<210> SEQ ID NO 13

```
<211> LENGTH: 33
<212> TYPE: DNA
<213> ORGANISM: Artificial Sequence
<220> FEATURE:
<223> OTHER INFORMATION: Synthetic Construct

<400> SEQUENCE: 13
tacctggttg atcctgccag tagcatatgc ttg                                    33

<210> SEQ ID NO 14
<211> LENGTH: 32
<212> TYPE: DNA
<213> ORGANISM: Artificial Sequence
<220> FEATURE:
<223> OTHER INFORMATION: Synthetic Construct

<400> SEQUENCE: 14
tttaatgagc cattcgcagt ttcactgtac cg                                     32

<210> SEQ ID NO 15
<211> LENGTH: 23
<212> TYPE: DNA
<213> ORGANISM: Artificial Sequence
<220> FEATURE:
<223> OTHER INFORMATION: Synthetic Construct

<400> SEQUENCE: 15
ccaacgtggc taagaatgtc atc                                               23

<210> SEQ ID NO 16
<211> LENGTH: 21
<212> TYPE: DNA
<213> ORGANISM: Artificial Sequence
<220> FEATURE:
<223> OTHER INFORMATION: Synthetic Construct

<400> SEQUENCE: 16
tgggcattgg tgttgtacgt c                                                 21

<210> SEQ ID NO 17
<211> LENGTH: 21
<212> TYPE: DNA
<213> ORGANISM: Artificial Sequence
<220> FEATURE:
<223> OTHER INFORMATION: Synthetic Construct

<400> SEQUENCE: 17
tggttaatct ccgcaggtca c                                                 21

<210> SEQ ID NO 18
<211> LENGTH: 22
<212> TYPE: DNA
<213> ORGANISM: Artificial Sequence
<220> FEATURE:
<223> OTHER INFORMATION: Synthetic Construct

<400> SEQUENCE: 18
actgtgctga agaggctgtt tg                                                22

<210> SEQ ID NO 19
<211> LENGTH: 23
<212> TYPE: DNA
<213> ORGANISM: Artificial Sequence
<220> FEATURE:
<223> OTHER INFORMATION: Synthetic Construct

<400> SEQUENCE: 19
```

```
gcgattcctt cactgataca ctg                                              23

<210> SEQ ID NO 20
<211> LENGTH: 23
<212> TYPE: DNA
<213> ORGANISM: Artificial Sequence
<220> FEATURE:
<223> OTHER INFORMATION: Synthetic Construct

<400> SEQUENCE: 20
gagtgggagt ggtcttccat tac                                              23

<210> SEQ ID NO 21
<211> LENGTH: 25
<212> TYPE: DNA
<213> ORGANISM: Artificial Sequence
<220> FEATURE:
<223> OTHER INFORMATION: Synthetic Construct

<400> SEQUENCE: 21
aagaagcagc aaaatgtacc tgaag                                            25

<210> SEQ ID NO 22
<211> LENGTH: 23
<212> TYPE: DNA
<213> ORGANISM: Artificial Sequence
<220> FEATURE:
<223> OTHER INFORMATION: Synthetic Construct

<400> SEQUENCE: 22
cctgattggt atgggtttca ctc                                              23
```